(12) United States Patent
Conway et al.

(10) Patent No.: US 7,837,633 B2
(45) Date of Patent: Nov. 23, 2010

(54) LANCING DEVICE AND MULTI-LANCET CARTRIDGE

(75) Inventors: William E. Conway, Smyrna, GA (US); Christopher J. Ruf, Marietta, GA (US); John C. Irwin, Woodstock, GA (US); Stephen J. Flynn, Peachtree City, GA (US); Avi M. Robbins, Longwood, FL (US); Brian D. Vanhiel, Smyrna, GA (US); Brian D. Leutz, McDonough, GA (US); Richard W. LeVaughn, Newnan, GA (US); Michael V. Lipoma, Villa Rica, GA (US); Bradley Koeppel, Smyrna, GA (US); David Andel, Lawrenceville, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 900 days.

(21) Appl. No.: 11/571,378

(22) PCT Filed: Jun. 30, 2005

(86) PCT No.: PCT/US2005/023155

§ 371 (c)(1),
(2), (4) Date: Dec. 28, 2006

(87) PCT Pub. No.: WO2006/004859

PCT Pub. Date: Jan. 12, 2006

(65) Prior Publication Data

US 2008/0119883 A1     May 22, 2008

Related U.S. Application Data

(60) Provisional application No. 60/584,115, filed on Jun. 30, 2004.

(51) Int. Cl.
    *A61B 5/00*             (2006.01)
    *A61B 17/32*           (2006.01)
    *A61B 17/14*           (2006.01)
    *B65D 81/00*          (2006.01)

(52) U.S. Cl. .................. 600/583; 600/573; 606/167; 606/181

(58) Field of Classification Search ......... 600/573–584; 606/167–183
See application file for complete search history.

(56) References Cited

U.S. PATENT DOCUMENTS 3,760,809 A     9/1973     Campbell, Jr.

(Continued)

FOREIGN PATENT DOCUMENTS

FR            2797579        2/2001
JP            2000245715 A    9/2000

*Primary Examiner*—Max Hindenburg
*Assistant Examiner*—Jeffrey G Hoekstra
(74) *Attorney, Agent, or Firm*—Gardner Groff Greenwald & Villanueva, PC

(57) ABSTRACT

A medical lancing device including a replaceable multi-lancet cartridge. The lancing device includes a drive mechanism, an activation mechanism, and an advancing mechanism. The advancing mechanism includes a linear-pull slide that is moved in and out to operate an indexing ratchet mechanism, a cam-guided charger mechanism, and a cam-guided lancet cap displacement mechanism. The indexing ratchet mechanism sequentially advances the lancets in the cartridge to an active position. The cam-guided charger mechanism charges the drive mechanism and separates the cap from the active lancet. And the cam-guided cap displacement mechanism moves the separated cap from the lancing stroke path of the active lancet. The activation mechanism then releases the charged active lancet to traverse the unobstructed lancing stroke path to pierce the subject's skin at a desired lancing site.

29 Claims, 31 Drawing Sheets

U.S. PATENT DOCUMENTS

| | | |
|---|---|---|
| D228,815 S | 10/1973 | Campbell, Jr. |
| D245,040 S | 7/1977 | Thomas |
| 4,643,189 A | 2/1987 | Mintz |
| D297,978 S | 10/1988 | White |
| 4,794,926 A | 1/1989 | Munsch et al. |
| 4,823,806 A | 4/1989 | Bajada |
| 4,892,097 A | 1/1990 | Ranalletta et al. |
| 4,983,178 A | 1/1991 | Schnell |
| 4,995,402 A | 2/1991 | Smith et al. |
| 5,047,044 A | 9/1991 | Smith et al. |
| 5,196,025 A | 3/1993 | Ranalletta et al. |
| 5,318,583 A | 6/1994 | Rabenau et al. |
| 5,318,584 A | 6/1994 | Lange et al. |
| 5,395,388 A | 3/1995 | Schraga |
| 5,464,418 A | 11/1995 | Schraga |
| 5,477,209 A | 12/1995 | Benson, Jr. et al. |
| 5,507,288 A | 4/1996 | Bocker et al. |
| 5,514,152 A | 5/1996 | Smith |
| 5,527,334 A | 6/1996 | Kanner et al. |
| 5,535,743 A | 7/1996 | Backhaus et al. |
| 5,551,422 A | 9/1996 | Simonsen et al. |
| D376,203 S | 12/1996 | Schraga |
| 5,628,764 A | 5/1997 | Schraga |
| 5,645,555 A | 7/1997 | Davis et al. |
| 5,676,143 A | 10/1997 | Simonsen et al. |
| 5,692,504 A | 12/1997 | Essenpreis et al. |
| 5,710,630 A | 1/1998 | Essenpreis et al. |
| 5,713,352 A | 2/1998 | Essenpreis et al. |
| 5,734,587 A | 3/1998 | Backhaus et al. |
| RE35,803 E | 5/1998 | Lange et al. |
| 5,770,454 A | 6/1998 | Essenpreis et al. |
| 5,776,157 A | 7/1998 | Thorne et al. |
| 5,786,226 A | 7/1998 | Bocker et al. |
| 5,825,488 A | 10/1998 | Kohl et al. |
| 5,879,373 A | 3/1999 | Roper et al. |
| 5,962,852 A | 10/1999 | Knuettel et al. |
| 5,971,941 A | 10/1999 | Simons et al. |
| 5,986,770 A | 11/1999 | Hein et al. |
| 5,997,561 A | 12/1999 | Bocker et al. |
| 6,010,519 A | 1/2000 | Mawhirt et al. |
| 6,036,924 A | 3/2000 | Simons et al. |
| 6,042,595 A | 3/2000 | Morita |
| 6,071,294 A | 6/2000 | Simons et al. |
| 6,093,156 A | 7/2000 | Cunningham et al. |
| 6,144,449 A | 11/2000 | Knuettel et al. |
| 6,156,050 A | 12/2000 | Davis et al. |
| 6,168,606 B1 | 1/2001 | Levin et al. |
| 6,210,421 B1 | 4/2001 | Bocker et al. |
| 6,228,100 B1 | 5/2001 | Schraga |
| D444,557 S | 7/2001 | Levaughn et al. |
| D447,566 S | 9/2001 | Levaughn et al. |
| 6,306,152 B1 | 10/2001 | Verdonk et al. |
| 6,330,063 B1 | 12/2001 | Knuettel et al. |
| D458,127 S | 6/2002 | De Groote |
| 6,418,339 B1 | 7/2002 | Essenpreis et al. |
| 6,432,120 B1 | 8/2002 | Teo |
| 6,472,220 B1 | 10/2002 | Simons et al. |
| 6,531,702 B1 | 3/2003 | Mischler et al. |
| 6,540,675 B2 | 4/2003 | Aceti et al. |
| 6,584,335 B1 | 6/2003 | Haar et al. |
| 6,616,616 B2 | 9/2003 | Fritz et al. |
| 6,706,159 B2 | 3/2004 | Moerman et al. |
| 6,783,537 B1 | 8/2004 | Kuhr et al. |
| 6,852,119 B1 | 2/2005 | Abulhaj et al. |
| 6,929,649 B2 | 8/2005 | Pugh |
| 6,966,880 B2 | 11/2005 | Boecker et al. |
| 6,988,996 B2 | 1/2006 | Roe et al. |
| 7,001,344 B2 | 2/2006 | Freeman et al. |
| 7,025,774 B2 | 4/2006 | Freeman et al. |
| 7,041,068 B2 | 5/2006 | Freeman et al. |
| 7,141,058 B2 | 11/2006 | Briggs et al. |
| 2002/0052618 A1 | 5/2002 | Haar et al. |
| 2002/0120216 A1 | 8/2002 | Fritz et al. |
| 2002/0130042 A1 | 9/2002 | Moerman et al. |
| 2002/0168290 A1 | 11/2002 | Yuzhakov et al. |
| 2003/0013992 A1 | 1/2003 | Uchigaki et al. |
| 2003/0073089 A1 | 4/2003 | Mauze et al. |
| 2003/0073931 A1 | 4/2003 | Boecker et al. |
| 2003/0083685 A1 | 5/2003 | Freeman et al. |
| 2003/0083686 A1 | 5/2003 | Freeman et al. |
| 2003/0088191 A1 | 5/2003 | Freeman et al. |
| 2003/0143113 A2 | 7/2003 | Yuzhakov et al. |
| 2003/0144608 A1 | 7/2003 | Kojima et al. |
| 2003/0144609 A1 | 7/2003 | Kennedy |
| 2003/0153939 A1 | 8/2003 | Fritz et al. |
| 2003/0185713 A1 | 10/2003 | Leonard et al. |
| 2003/0199789 A1 | 10/2003 | Boecker et al. |
| 2003/0199790 A1 | 10/2003 | Boecker et al. |
| 2003/0199791 A1 | 10/2003 | Boecker et al. |
| 2003/0199893 A1 | 10/2003 | Boecker et al. |
| 2003/0199894 A1 | 10/2003 | Boecker et al. |
| 2003/0199895 A1 | 10/2003 | Boecker et al. |
| 2003/0199896 A1 | 10/2003 | Boecker et al. |
| 2003/0199897 A1 | 10/2003 | Boecker et al. |
| 2003/0199898 A1 | 10/2003 | Boecker et al. |
| 2003/0199899 A1 | 10/2003 | Boecker et al. |
| 2003/0199900 A1 | 10/2003 | Boecker et al. |
| 2003/0199901 A1 | 10/2003 | Boecker et al. |
| 2003/0199902 A1 | 10/2003 | Boecker et al. |
| 2003/0199903 A1 | 10/2003 | Boecker et al. |
| 2003/0199904 A1 | 10/2003 | Boecker et al. |
| 2003/0199905 A1 | 10/2003 | Boecker et al. |
| 2003/0199906 A1 | 10/2003 | Boecker et al. |
| 2003/0199907 A1 | 10/2003 | Boecker et al. |
| 2003/0199908 A1 | 10/2003 | Boecker et al. |
| 2003/0199909 A1 | 10/2003 | Boecker et al. |
| 2003/0199910 A1 | 10/2003 | Boecker et al. |
| 2003/0199911 A1 | 10/2003 | Boecker et al. |
| 2003/0211619 A1 | 11/2003 | Olson et al. |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0212424 A1 | 11/2003 | Briggs et al. |
| 2003/0223906 A1 | 12/2003 | McAllister et al. |
| 2004/0009100 A1 | 1/2004 | Simons et al. |
| 2004/0010279 A1 | 1/2004 | Freeman et al. |
| 2004/0039303 A1 | 2/2004 | Wurster et al. |
| 2004/0049219 A1 | 3/2004 | Briggs et al. |
| 2004/0049220 A1 | 3/2004 | Boecker et al. |
| 2004/0064068 A1 | 4/2004 | DeNuzzio et al. |

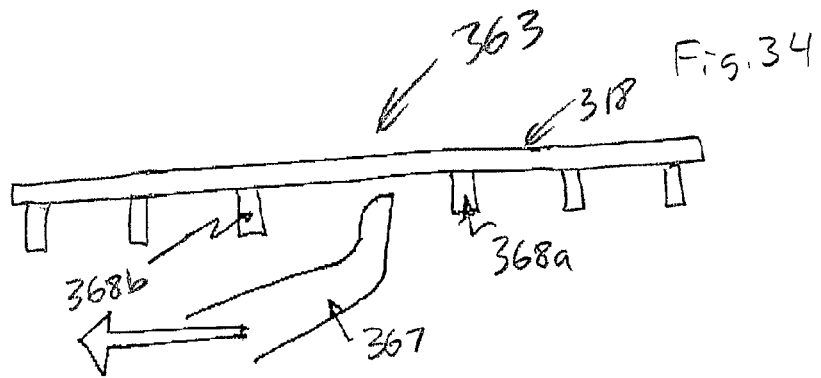
Fig. 34
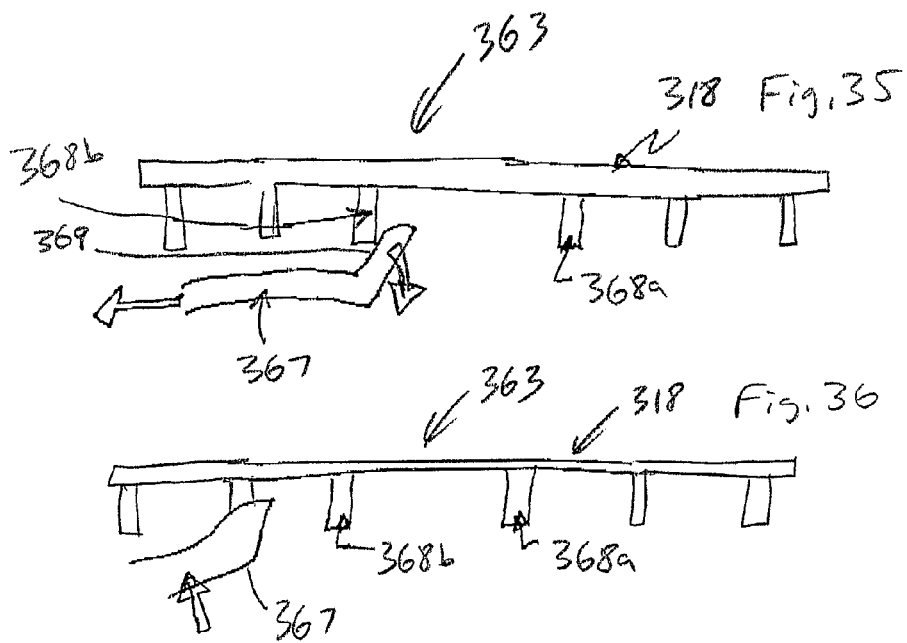
Fig. 35
Fig. 36
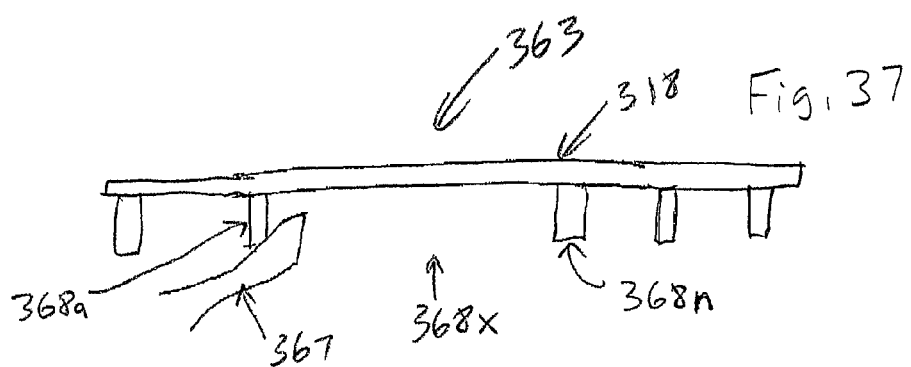
Fig. 37

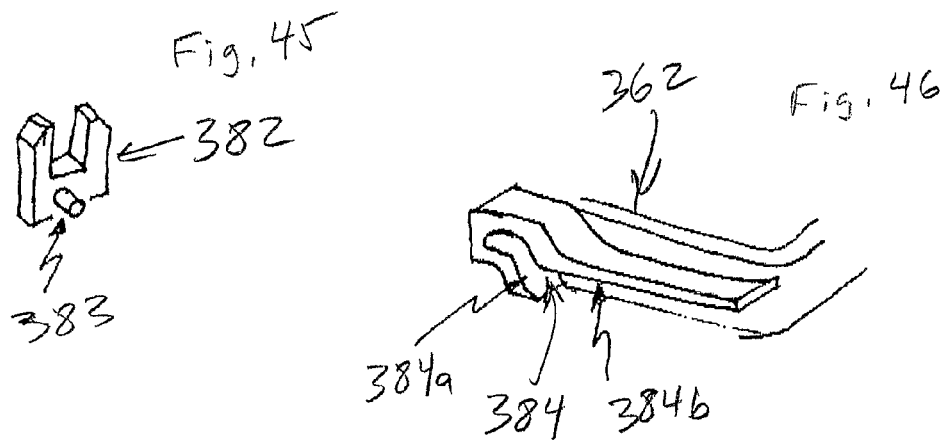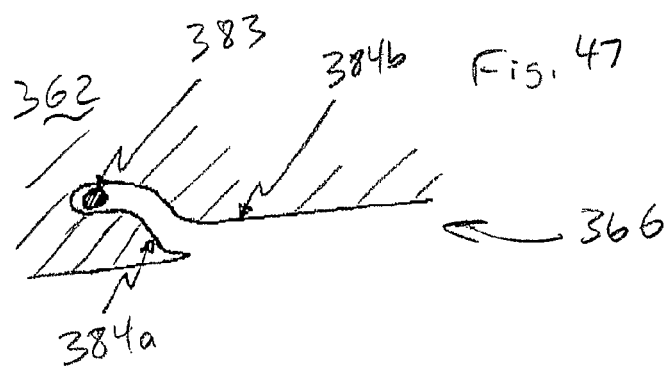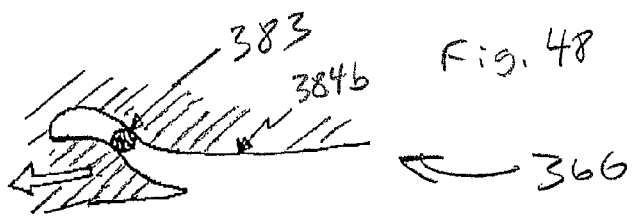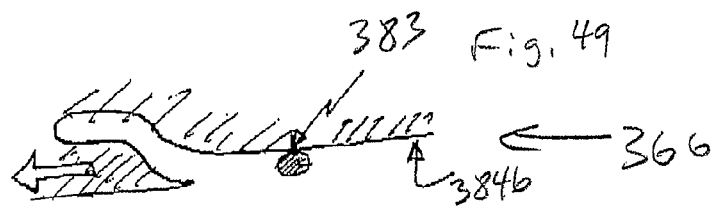

LANCING DEVICE AND MULTI-LANCET CARTRIDGE

CROSS REFERENCE TO RELATED APPLICATION

This applications claims priority to U.S. Provisional Patent Application Ser. No. 60/584,115, filed Jun. 30, 2004, which is hereby incorporated herein by reference its entirety.

TECHNICAL FIELD

The present invention relates generally to medical devices and procedures, and more particularly to cartridge assemblies for lancing devices for the collection and/or analysis of samples of blood or other bodily fluids.

BACKGROUND OF THE INVENTION

Many medical procedures require puncturing of the skin, and sometimes underlying tissues, of an animal or human subject. For example, a sharp lancet tip is commonly used to puncture the subject's skin at a lancing site to obtain a sample of blood, interstitial fluid or other body fluid, as for example in blood glucose monitoring by diabetics and in blood typing and screening applications.

In some instances, a person must periodically sample their blood for multiple testing throughout the day or week. Because re-use of a lancet can result in infection or spread of blood borne contaminants, persons requiring repeated testing often must carry multiple lancets with them, which are separately loaded into a lancing device for each sampling. This can be inconvenient and may lead to reduced compliance with a prescribed test regimen.

Accordingly, it has been discovered that needs exist for an improved lancing device capable of carrying out multiple sampling procedures without the need for separately loading individual lancets. It has also been discovered that needs exist for a convenient, disposable multi-lancet cartridge that can be loaded into a multi-use lancing device for carrying out multiple sampling procedures, and be removed and replaced when fully or partially spent or when replacement is otherwise desired. It is to the provision of an improved sampling device and cartridge meeting these and other needs that the present invention is primarily directed.

SUMMARY OF THE INVENTION

Briefly described, in one aspect, the present invention is a lancing device comprising an outer housing for receiving a replaceable cartridge. Preferably, the cartridge includes a static outer shell that remains stationary relative to the housing and drive mechanism of the lancing device, and an array of lancets that are rotationally advanced within the outer shell and sequentially indexed through an active position for carrying out multiple lancing procedures. The cartridge preferably includes a rotationally moveable carrier for retaining and rotationally advancing the radial array of lancets within the outer shell, and for constraining the active lancet along a controlled and pre-defined path of travel during the lancing stroke. The cartridge preferably also includes recesses, clips, or other retainers for retaining protective endcaps that have been removed from the lancets out of the path of travel of the lancets, and preventing the caps from rattling around within the housing.

The lancing device preferably includes a drive mechanism, including for example a pair of opposed biasing mechanisms (e.g., springs) working in tandem, to drive and return the plunger mechanism of the lancing device and propel the active lancet through its lancing stroke. In example embodiments, the jaw of the drive mechanism engages the active lancet from the bottom only, through a slot in the cartridge shell, so that a partially spent cartridge can be removed from the lancing device and reinserted for use at a later time. In further example embodiments, the lancing device includes a one-way clutch or ratchet mechanism to advance lancets sequentially through the active position and to prevent re-use of lancets. The lancing device preferably also includes an advancing and charging mechanism for sequentially indexing the lancet carrier, charging the drive mechanism, and detaching the endcap of the lancet at a controlled retraction rate during de-capping, all with a single and continuous operation.

The lancing device optionally includes a depth ring for adjusting the depth of penetration of the lancet. Preferably, the depth ring has a plurality of openings with varying opening sizes and varying countersink depths, and is rotatable through a sequence of positions adjacent the lancet opening in the housing of the lancing device, thereby forming a rotating shutter window, providing a wide range of depth control. In further example embodiments, the lancing device includes an improved activating button operable to activate the drive mechanism, and including an integral spring arm for biasing the activating button outwardly and a retainer for securing the rotating depth ring.

In another aspect, the invention is an improved cartridge assembly for use with a multi-use lancing device. The cartridge assembly preferably includes a plurality of penetration elements or lancets, each having its own protective covering or endcap, arranged for sequential use in piercing the skin or other tissue of a human or animal subject for obtaining a sample of blood, interstitial fluid, and/or other body fluid(s). In example embodiments, the cartridge has an outer shell or housing and a carrier assembly rotationally enclosed within the outer shell for retaining the lancets. Because the carrier rotationally advances the lancets within the outer shell of the cartridge, only one opening through the shell is required for allowing passage of the active lancet tip upon actuation of the device, thereby reducing the potential for contamination or accidental needle sticks.

In yet another aspect, the present invention is a cap displacement mechanism that moves a sterility cap, after it has been separated from the active lancet, out of the lancing stroke travel path of the active lancet. In a first example embodiment, the cartridge includes a cantilevered spring arm that is mounted within the cartridge shell to bias the separated lancet cap out of the path of the lancing stroke. In a second example embodiment, the lancing device includes a spring-biased plunger that is driven along a cam surface of the lancing device to engage a lancet cap and push it transversely out of the path of the lancing stroke. In both embodiments, the carrier defines transverse guide paths near its outer perimeter for directing and retaining the lancet caps out of the travel path of the lancet tip. The transverse guide paths are preferably defined by one or more guide tracks (e.g., resilient fingers, barbs, or other engagement features) extending from the carrier for positively retaining the lancet caps that have been removed from the lancet bodies.

And in still another aspect, the present invention is a linear-pull advancing mechanism that replaces the rotational cam drive advancing mechanism and the cap displacement mechanism previously described. In an example embodiment, the advancing mechanism includes a linear-pull slider that is moved in and out to operate an indexing ratchet mechanism, a cam-guided charger mechanism, and a cam-guided lancet cap displacement mechanism. The indexing ratchet mechanism includes a resilient pawl extending from the slider and a plurality of ratchet teeth extending downward from the lancet carrier for sequentially advancing the lancets in the cartridge to an active position. The cam-guided charger mechanism includes a cam arm that is resiliently deflected by a follower on the drive plunger and then guides the piston for charging the drive mechanism and separating the cap from the active lancet. And the cam-guided cap displacement mechanism includes a lifter with a follower that rides along a cam surface for moving the separated cap from the lancing stroke path of the active lancet. The activation mechanism then releases the charged active lancet to traverse the unobstructed lancing stroke path to pierce the subject's skin at a desired lancing site.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 9 is a side view of the advancer mechanism of FIG. 6, showing the spring-biased cam-driven plunger reset to a position clear of the lancing stroke travel path.

FIG. 15b is a detailed plan view of the advancer mechanism of FIG. 6, including the portion shown in FIG. 15a.

FIG. 34 is a side view of the ratchet mechanism of FIG. 30, showing the pawl being retracted as the slider is pushed/retracted.

FIG. 35 is a side view of the ratchet mechanism of FIG. 30, showing the pawl retracted into engagement with, and resiliently deflecting under, a next tooth.

FIG. 36 is a side view of the ratchet mechanism of FIG. 30, showing the pawl fully retracted as the slider is moved to the retracted position of FIG. 17.

FIG. 37 is a side view of the ratchet mechanism of FIG. 36, showing the ratchet mechanism after all of the lancets in the cartridge have been used.

FIG. 45 is a perspective view of a lifter member of a cam-guided lancet cap displacement mechanism of the advancer mechanism of the lancing device of FIG. 17.

FIG. 46 is a perspective view of a cam surface of the cam-guided lancet cap displacement mechanism of the advancer mechanism of the lancing device of FIG. 17.

FIG. 47 is a side view of a portion of the cam-guided cap displacement mechanism of FIGS. 45 and 46, showing a follower of the lifter raised by its engagement with the cam surface when the slider is in its retracted position of FIG. 17.

FIG. 48 is a side view of the cam-guided cap displacement mechanism of FIG. 47, showing the lifter follower guided downward along the cam surface as the slider is pulled/extended.

FIG. 49 is a side view of the cam-guided cap displacement mechanism of FIG. 47, showing the lifter follower riding further along the cam surface as the slider is pulled/extended further.

DETAILED DESCRIPTION OF EXAMPLE EMBODIMENTS

Figure 1:
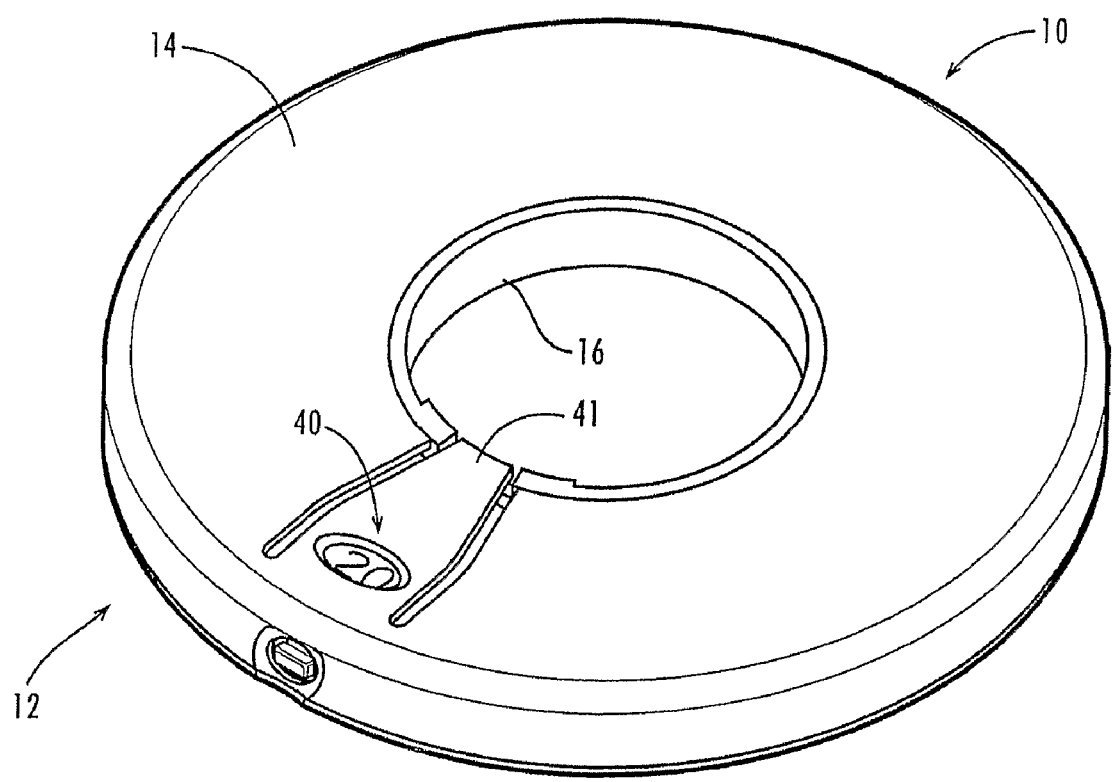
FIG. 1 is a perspective view of a multi-lancet cartridge assembly for a lancing device in accordance with a first example embodiment of the present invention.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

In its various embodiments, the present invention relates to multi-lancet lancing devices having multi-lancet cartridges, disposable multi-lancet cartridges for use in the lancing devices, and reusable lancing device housings for holding the multi-lancet cartridges. The subject matter of the present invention relates primarily to the improved advancer mechanism described in section 4 of this specification. The numbered preceding sections of the specification provide details of the multi-lancet cartridge and lancing device, which are improved by including the advancer mechanism.

The improvements of the present invention are adaptable for application in connection with various forms of multi-lancet lancing devices. In particular, the improvements of the present invention are of potential application to the multi-lancet lancing devices and replaceable multi-lancet cartridges shown in PCT International Publication No. WO 03/071940 A1 (International Application No. PCT/US03/05159, filed Feb. 20, 2003), which is hereby incorporated herein by reference. It will be recognized that the improvements disclosed herein are of individual advantage, or can be used in combination with one another. That is, the indexing ratchet mechanism, the cam-guided charger mechanism, and the cam-guided cap displacement mechanism described in section 4 can be implemented independently of each other in a lancing device including only one or any combination of these mechanisms. Or the cap displacement mechanisms described in sections 1.a. and 1.b. can be substituted in for the cap displacement mechanism described in section 4, and vice versa. Whichever of these mechanisms are included, they are preferably all operated by a single action such as the pull and push of one handle or other actuating member.

In general, the lancing device of the present invention comprises a housing defining a chamber for receiving the cartridge; a drive mechanism for propelling an active lancet of the cartridge through a lancing stroke, from a retracted position within the cartridge to an advanced position wherein a sharp tip of the active lancet projects through a lancet opening in the housing to pierce the subject's skin at an intended lancing site; a charging mechanism for energizing the drive mechanism; and an advancing mechanism for sequentially advancing lancets of the cartridge into and through the active position. Various of these mechanisms can be combined; for example, a single mechanism optionally serves to energize the drive mechanism and simultaneously or sequentially advance the cartridge.

It will be understood that the lancet cap displacement mechanisms of the present invention may be embodied in a variety of styles of lancet cartridges and lancing devices. For example, the cap displacement mechanisms can be adapted for use in a cartridge having a radial arrays of lancets (as described herein), a linear array of lancets, a cylindrical array of axially arranged lancets, or other lancet and carrier configurations. And the cap displacement mechanisms can be adapted for use in disposable multi-lancet lancing devices (without a replaceable cartridge), with the components of the cap displacement mechanisms being elements of the lancing devices.

1. The Cartridge Assembly

Figure 2:
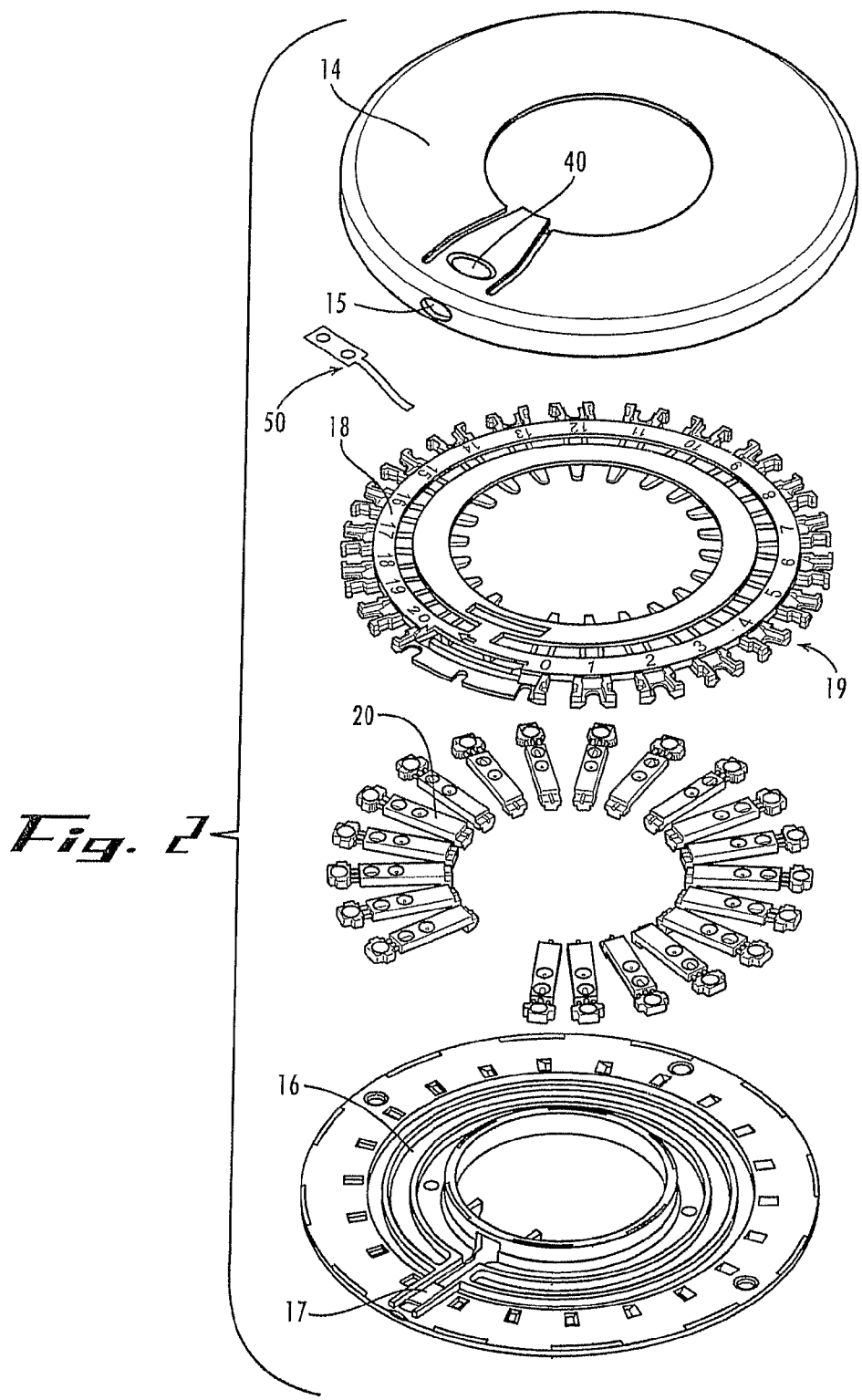
FIG. 2 is an exploded perspective view of the cartridge assembly of FIG. 1, showing a base housing, lancet array, carrier disk, spring-arm cap displacer, and cover housing.

With reference now to the drawing figures, FIGS. 1 and 2, as a perspective and exploded view respectively, show a cartridge assembly according to a first example embodiment of the present invention, which as a whole is designated by the reference number 10. The cartridge assembly 10 comprises a housing 12 for an array of lancets 20. The housing 12 preferably has two portions that connect together, for example, a top portion or cover 14 and a bottom portion or base 16. The top portion 14 and the bottom portion 16 preferably comprise generally circular disk-like structures with generally circular central aligned openings. The bottom portion 16 preferably has guides thereon or therein for engaging and guiding a rotatable carrier disk 18. When secured to together, the top portion 14 and the bottom portion 16 collectively form an annular outer shell of the cartridge assembly 10 for containing the carrier 18 and the array of lancets 20. In addition, the top cover 14 preferably defines a single lancet opening 15 on its outer circumferential rim, through which the tip of an active one of the lancets 20 passes during its lancing stroke.

The carrier disk 18 preferably includes guide channels 19 for permitting radial sliding movement of the lancets 20 in a lancing stroke between a retracted position and an extended position during the lancing operation. The guide channels 19 may be formed by projections on or recesses in the face of the carrier disk 18. In an example embodiment, the carrier 18 comprises twenty radial guide channels 19 for holding twenty lancets 20. The carrier 18 may, however, be provided with more or less guide channels 19 and lancets 20, as desired.

The lancets 20 are radially arranged in the rotatable carrier disk 18 in the guide channels 19, and can be driven through their lancing strokes in their axial direction (i.e., along a radius of the carrier disk 18) upon actuation of the lancing device. The cartridge assembly 10 is arranged such that the carrier disk 18, loaded with the lancets 20, is rotatably mounted on the bottom portion 16 of the housing 12. The top portion 14 of the housing 12 is then secured to the bottom portion 16, for example by ultrasonic welding, such that the carrier disk 18 and the lancets 20 can rotate within the housing 12. A one-way clutch or ratchet mechanism preferably limits the rotation of the carrier disk to rotation in a single direction to prevent re-use of a lancet and resultant potential contamination.

Figure 3:
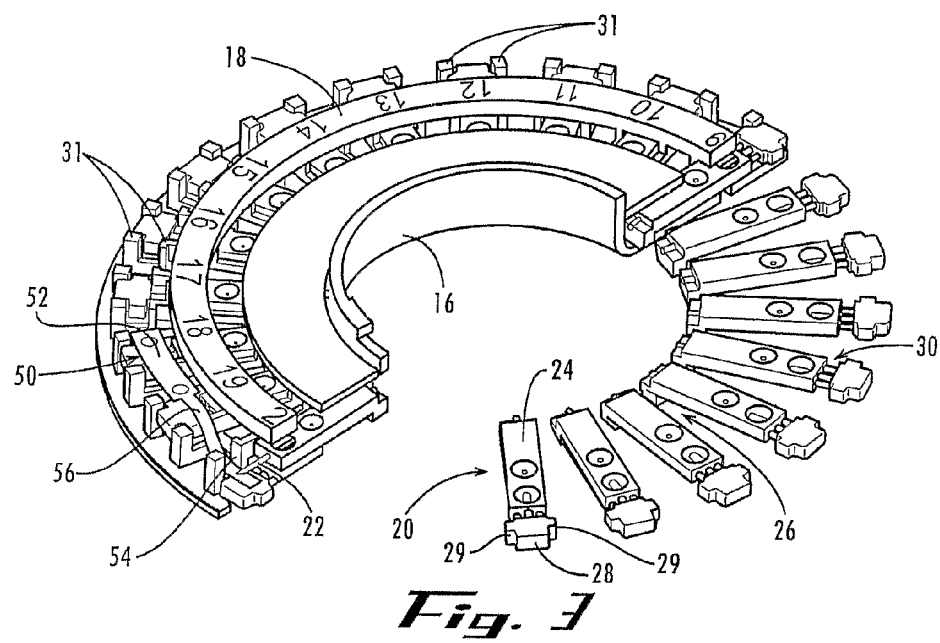
FIG. 3 is a cutaway perspective view of the lancet array, carrier, and spring arm of FIG. 2, showing spring arm displacing a separated cap of an active lancet.
Figure 4:
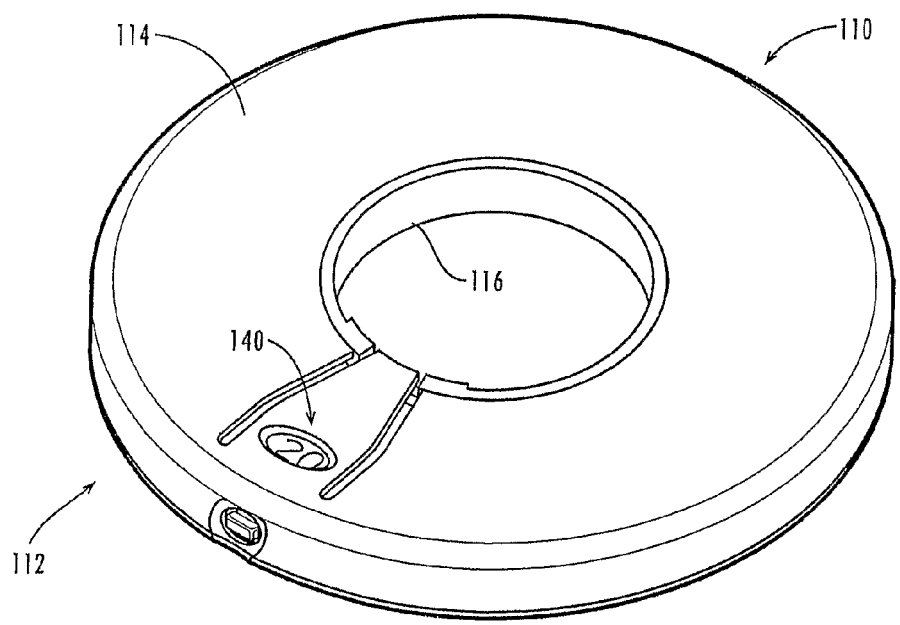
FIG. 4 is a perspective view of a cartridge assembly for a lancing device in accordance with a second example embodiment of the present invention.
Figure 5:
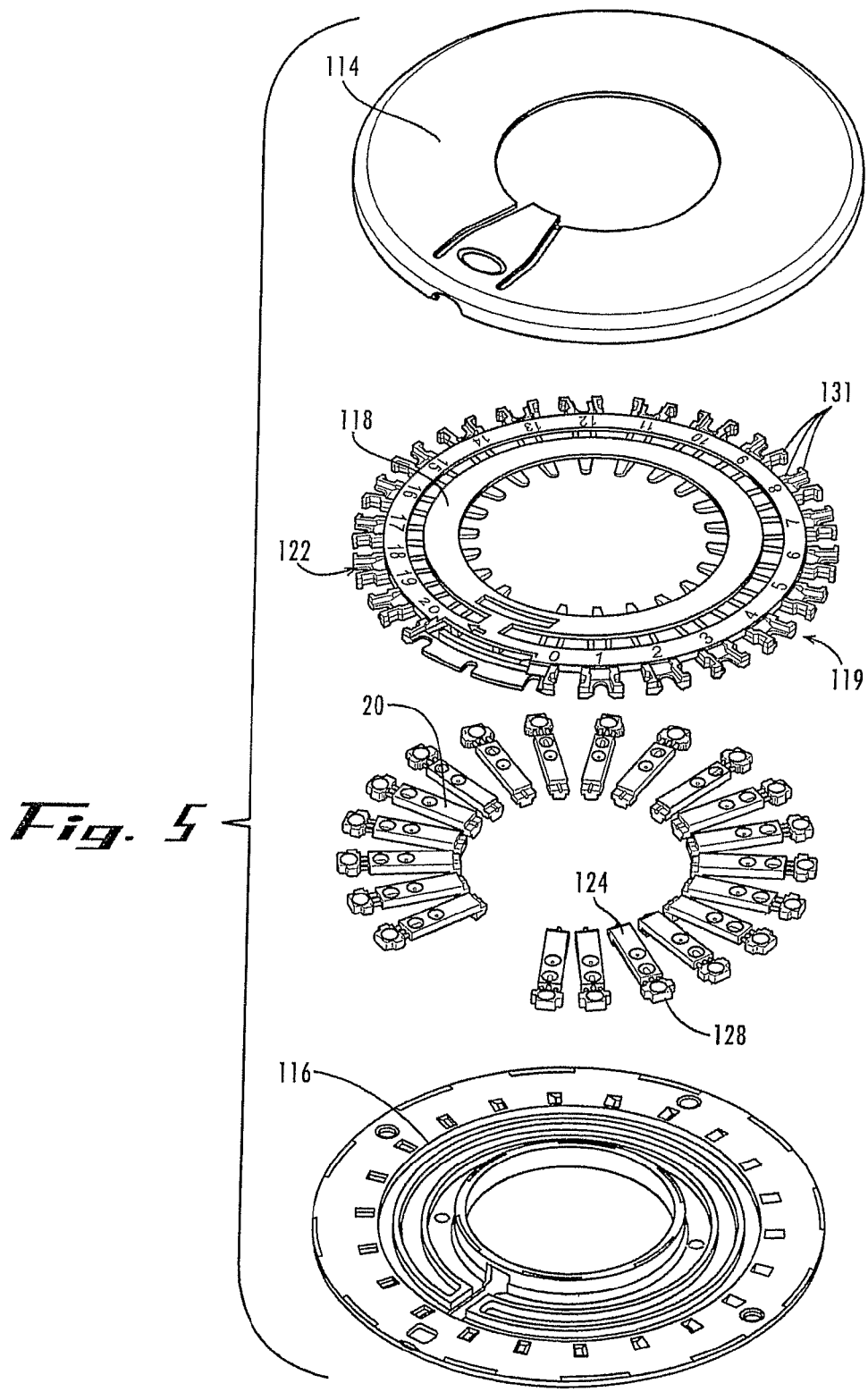
FIG. 5 is an exploded perspective view of the cartridge assembly of FIG. 4, showing a base housing, lancet array, carrier disk, and cover housing.

Referring additionally to FIG. 3, the lancets 20 each preferably comprise a needle or blade forming a sharp lancet tip 22, and a lancet body 24, and are preferably arranged generally radially in the guide channels 19 of the carrier disk 18 with their tips 22 directed outwardly. Preferably, the lancet body 24 is formed of plastic and is injection-molded around the lancet tip 22. Each lancet tip 22 is preferably encapsulated by a protective endcap 28, which may be integrally molded with the lancet body 24 and forms a sterility and safety barrier for the lancet tip.

The protective cap 28 of each lancet 20 is preferably connected to the body 24 by one or more thin segments or a reduced-thickness transition region such as a notch or slit, which forms a weaker separation zone that gives easily so that the cap can be removed. When the lancing device is charged or cocked (i.e., when the plunger of the drive mechanism pulls the lancet body 24 radially inwardly to energize the drive mechanism), the separation zone 30 fails and allows the protective cap 28 to easily detach from the lancet body 24. Alternatively, for lancets having caps that are discrete structures, the separation zone is defined by the gap between the cap and the lancet body.

Each lancet body 24 has a retainer that engages a cooperating structure of the lancing device's drive mechanism (described below) when the lancet is in the active position. For example, each lancet body 24 may have a retainer foot 26 extending downward from the back of the lancet body 24 to engage a cooperating jaw or other structure of the drive mechanism's reciprocating plunger when the lancet is in the active position. The feet 26 of the lancets 20 that are not in the active position preferably slide within a curved foot channel in the cartridge bottom housing 16 to constrain the used lancets against movement in the radial direction unless the lancet is in the active position.

The cartridge bottom housing 16 preferably defines a radial lancing channel 17 extending from the curved foot channel at a position corresponding to the lancet opening 15 in the cartridge top housing 14. The active lancet slides in the lancing channel 17 as it is driven along the lancing stroke upon activation or firing of the lancing device.

One or more cap surfaces 29 are engaged and constrained by cooperating cap guide tracks 31 of the carrier 18. The cap surfaces 29 may be defined by two shoulders projecting laterally outwardly on opposite sides of the cap 28, as shown, or by other features such as recesses formed into the caps. The cap guide tracks 31 hold unused lancets 20 in position on the carrier 18 prior to use, and to hold the cap 28 as the active lancet body 24 is retracted upon charging or energizing of the drive mechanism to detach the cap. The cap guide tracks 31 preferably define a transverse guide path (i.e., out of the plane of the lancet array, preferably at about 90 degrees relative to the lancing stroke travel path) along which the cap 28 is moved after it is detached from the lancet body 24. This transverse guide path allows removal of the cap 28 from the path of travel of the active lancet 20 as it is driven through its lancing stroke upon activation. The cap guide tracks 31 preferably comprise one or more resilient fingers or barbs for guiding the detached cap 28 along the transverse guide path and retaining the cap in its transversely displaced position so that it is prevented from rattling around within the housing 12 or potentially interfering with the device's operation. As an example, four cap guide track fingers 31 may be provided for receiving and guiding the two cap shoulder surfaces 29, as shown. Alternatively, two cap guide track fingers may be provided for guiding and being received by two cap recessed surfaces.

As shown in FIGS. 1 and 3, the carrier disk 18 can optionally be labeled with numbers or other indicia to indicate the number of unused lancets 20 remaining (or alternatively the number of lancets already used). The cartridge housing 12 preferably has an opening 40 therethrough, and the lancing device has a corresponding opening, such that the user can view the indicia.

The cartridge 10 preferably has a resilient member that is biased into engagement with an underlying lancet 20 in the active position. The resilient member thus prevents said active lancet 20 from being displaced if the cartridge 10 is removed from the lancing device after the device is charged and the cap is detached, at which point the active lancet would otherwise be unconstrained. The resilient member preferably comprises a resilient tongue portion 41 formed by a pair of cutout slots defined in the top housing cover 14 of the cartridge 10. When the cartridge 10 is installed in the lancing device, a cooperating portion of the drive mechanism flexes the tongue 41 out of contact with the active lancet, freeing it to traverse its lancing stroke upon actuation of the lancing device. In an alternate embodiment, the carrier is partially indexed within the cartridge housing (for example, a half-step forward or back, to a position between adjacent lancets), when the cartridge is removed from the lancing device, to prevent displacement of an unconstrained lancet from the active position.

a. Spring-Actuated Displacement of End-Caps

In this first example embodiment, the lancet cap displacement mechanism is provided by a cantilevered spring member 50 that serves to press the detached protective cap 28 of each sequential active lancet 20 along the transverse guide path and out of the radial path of travel of that lancet prior to activation or firing. The spring member 50 preferably has a first section 52, a second section 54, and an intermediate section 56. The first section 52 is attached (by conventional fastening structures or techniques) to the inner surface of the top portion 14 of the housing 12, or to another stationary part of the cartridge 10. The second section 54 is configured to engage the protective cap 28 and to push the cap 28 downwardly along the cap guide tracks 31 of the carrier 18, towards the bottom portion 16 of the housing 12. The intermediate section 56 connects the first section 52 to the second section 54.

In a typical commercial embodiment, the spring member 50 is leaf spring-type spring member, comprising a flexible, resilient piece of metal or other material that does not readily take on a set permanent deformation. The first section 52, the second section 54, and the intermediate section 56 each include an elongated member. And the intermediate section 56 is angled or curved downwardly from the first section 52 to the second section 54, thereby offsetting the first and second sections. In this way, the spring member 50 rides along the top surface of a lancet's endcap 28 as that lancet is advanced into the active position, and the spring member 50 flexes upwardly and is charged to impart a downward force on the cap. Then upon detachment of the cap 28 from the active lancet 20 by the retraction of the lancet body 24, the cap is pressed down along the guide tracks 31 under the influence of the charged spring member 50.

In an alternative embodiment, the leaf spring-type spring member 50 is inverted and attached to the housing bottom 16. In another alternative embodiment, the member 50 is a coil spring, with one end (the first section 52) attached to the housing 12 and the other end (the second section 54) including a ramped extension panel for riding along the caps as they are rotated to the active position.

b. Cam-Actuated Displacement of End-Caps

Referring now to FIGS. 4-9, a second example embodiment of the present invention will be described. The cartridge assembly 100 is substantially similar to the cartridge assembly 10 described above, having a housing 112 with top and bottom sections 114 and 116, a carrier 118, and an array of lancets 120 each having a body 124 and a cap 28.

Figure 6:
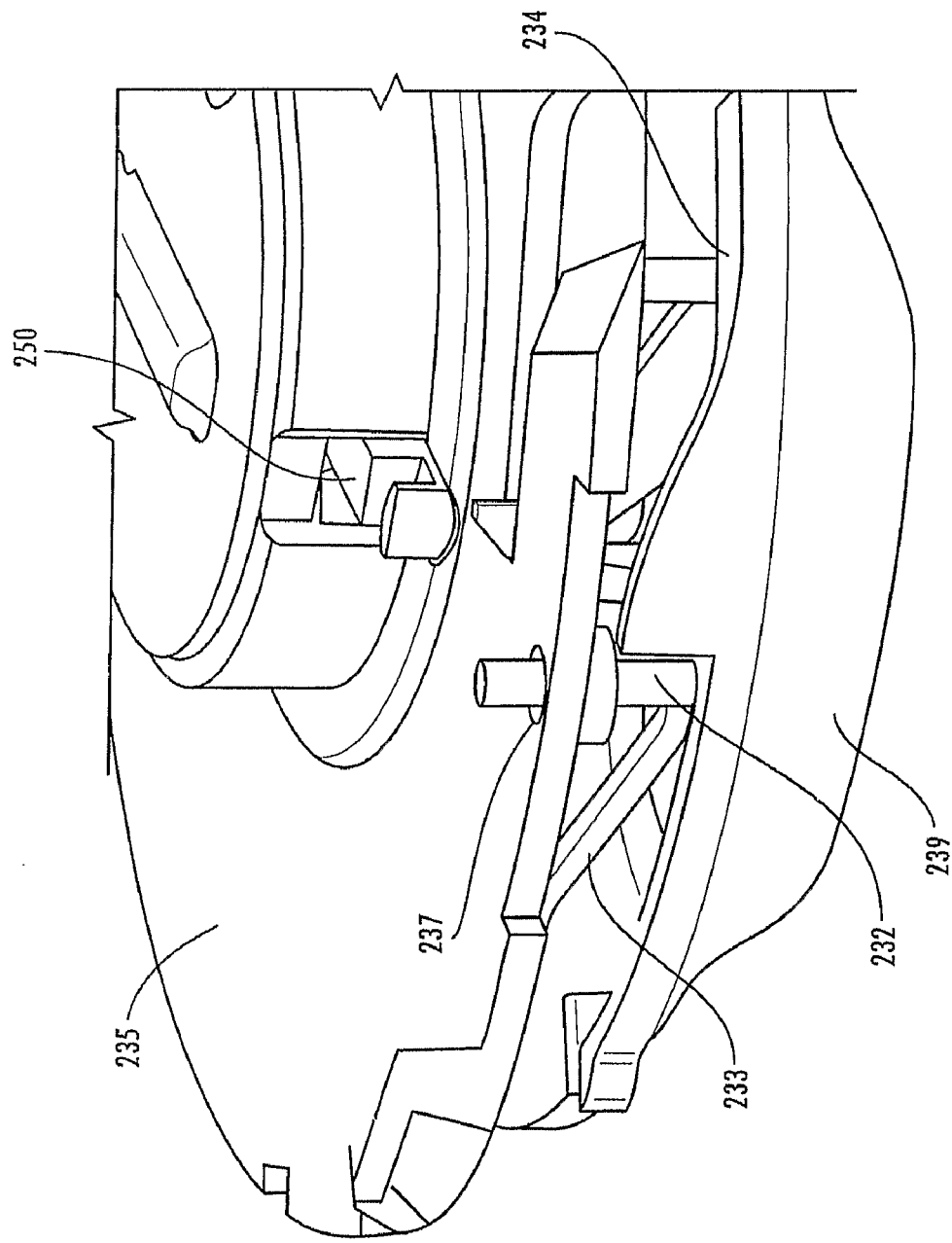
FIG. 6 is a partial perspective view of an advancer mechanism of the lancing device for use with the cartridge of FIG. 4, showing a spring-loaded cap-displacing plunger driven by a cam surface of the advancer mechanism.

In this embodiment, however, the lancet cap displacement mechanism is provided by a spring-biased cam-driven plunger assembly. This assembly includes a plunger 232 that is positioned at about the cartridge outer perimeter and adjacent (beneath or above) the active lancet position. The plunger 232 is in the form of a pin, shaft, tube, T-member, angle piece, or other elongated structure. With particular reference to FIGS. 6 and 9, the plunger 232 is ordinarily biased away from the active lancet (e.g., downwardly) under the influence of a spring element 233. The spring element 233 may be provided by a cantilevered leaf spring arm that is attached to (and integrally formed with) the plunger 232, as shown. Alternatively, the spring element may be provided by a coil spring (e.g., coaxially arranged with the plunger), an elastic member (e.g., rubber band), or other biasing structure. In the depicted embodiment, the plunger 232 extends through an opening 235 in the upper shell 237 of the advancing mechanism 230, and the spring element 233 is attached to the upper shell and the plunger.

The spring-biased cam-driven plunger assembly further comprises a cam surface 234 formed, for example, on the lower shell 239 of the advancer mechanism 230 of the lancing device. Preferably, the cam surface 234 is generally wedge-shaped, as shown, with two of the wedges arranged at about 180 degrees apart, though other specific shapes, numbers, and spacings of the cams may be used. As the advancer mechanism 230 is actuated, a follower surface of the plunger 232 traverses along the cam surface 234. The plunger 232 rises as it moves along the upwardly inclined portion of the cam surface 234, at the same time charging the spring arm 233. As the plunger 232 rises, it is pressed into engagement with the cap 128 of the active lancet 120. The rising plunger 232 pushes the cap 128 upwardly along the cap guide tracks 131 of the carrier disk 118 along the transverse guide path at about 90 degrees relative to the lancing stroke travel path, and out of the radial path of the active lancet's lancing stroke. The cap guide tracks 131 are preferably resilient members (e.g., barbs or fingers) that retain the cap 128 above the path of travel of the active lancet, as seen best with reference to FIG. 8. Continued actuation of the advancer mechanism 230 moves the inclined portion of the cam surface 234 past the plunger 232, as seen best with reference to FIG. 9, allowing the plunger to drop back down under the influence of the charged spring arm 233. The plunger 232 is now reset and out of the active lancet's path of travel as it is propelled along its lancing stroke.

It will be understood that the spring-biased, cam-driven plunger assembly may be provided as part of one or more other components of the lancing device. For example, in an alternative embodiment the spring and plunger are attached to and extend upwardly from the housing bottom with the spring biased upwardly to displace the lancet caps. And the cam surface is formed on a rotary element (e.g., rotationally moved by the advancing mechanism) within the lancing device housing. The cam surface may be configured to drive the plunger downwardly away from the active lancet cap except when the lancet is charged and ready for activation, at which position the plunger moves under the influence of the spring to displace the cap. For example, the cam surface may be defined by two (or another number of) upwardly recessed notches that permit the plunger to move upward to displace the caps. In other alternative embodiments, the cam surface is defined on a stationary element and the plunger is rotated relative to the cam surface for driving the plunger to displace the lancet caps.

2. The Lancing Device

Figure 16:
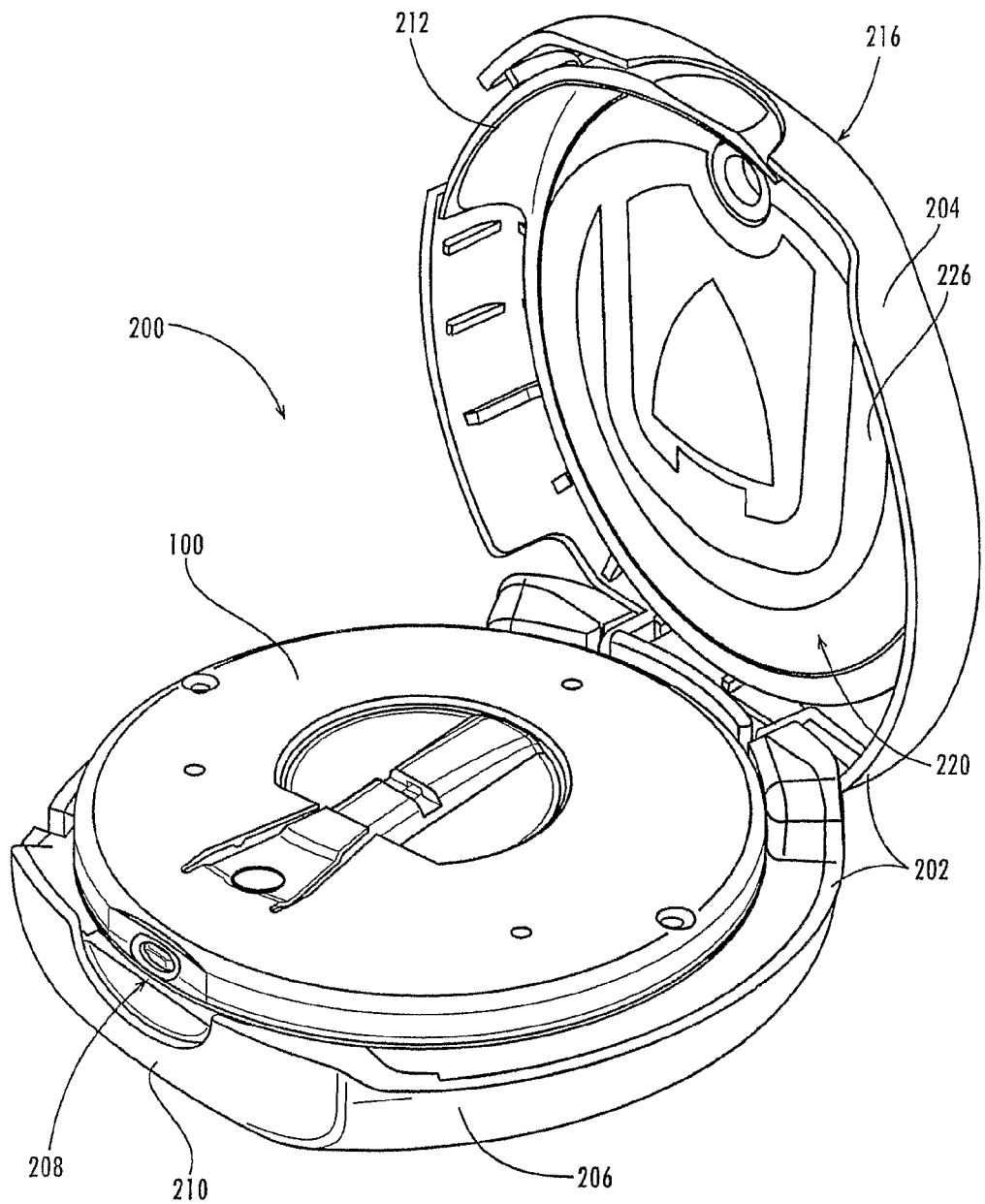
FIG. 16 is a perspective view of the cartridge of FIG. 4 installed in the lancing device of FIG. 7.

As shown in FIG. 16, a lancing device 200 according to an example embodiment of the present invention preferably comprises a clam-shell housing 202 having a top portion 204 hingedly connected to a bottom portion 206. The housing 202 defines a lancing opening 208, preferably through a sidewall portion 210 thereof, that aligns with the lancing opening 15 of an installed cartridge 100. The housing 202 preferably also comprises a latch 216 that secures the top 204 of the housing 202 to its bottom 206.

Figure 7:
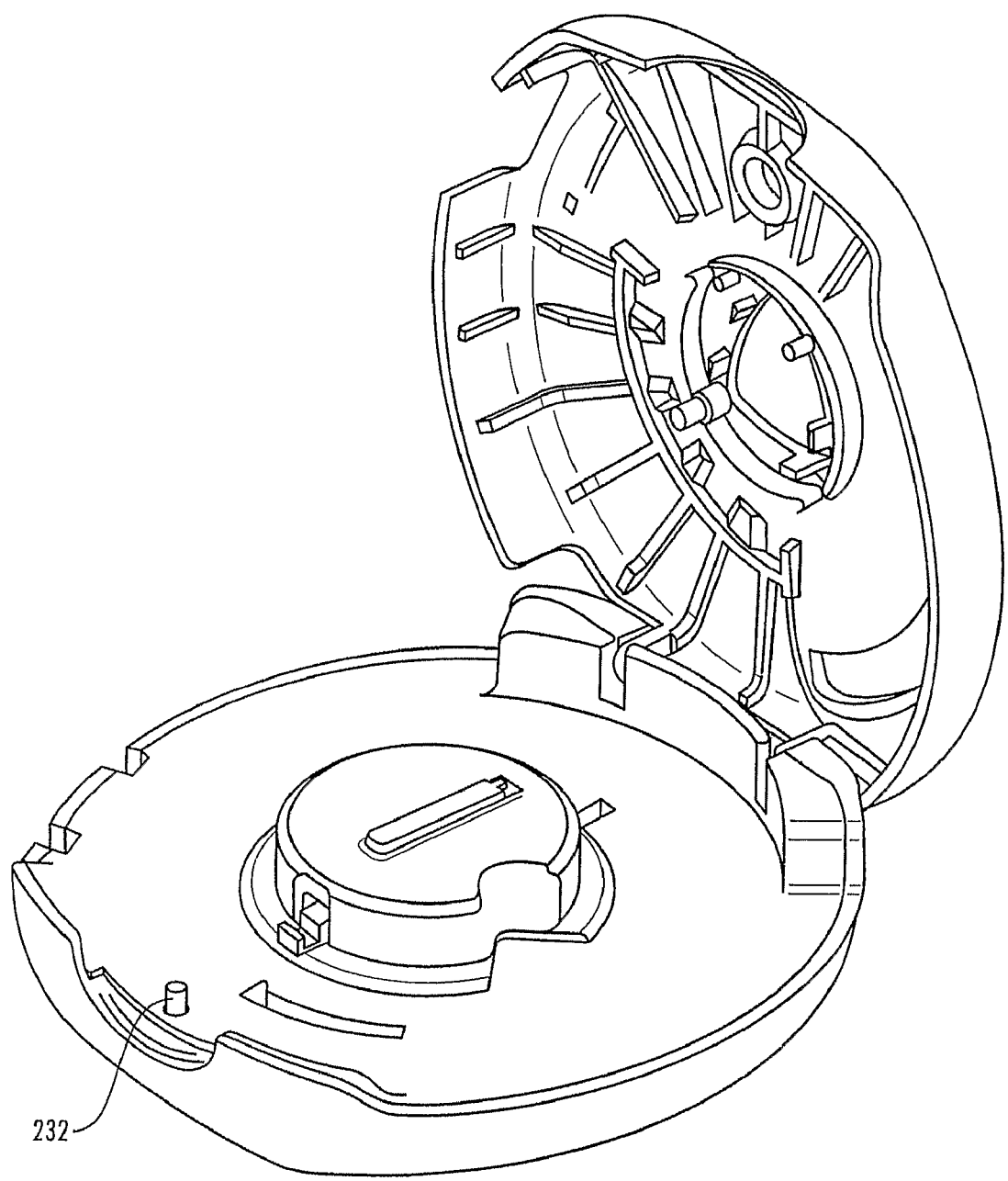
FIG. 7 is a perspective view of a lancing device according to the second example embodiment of the invention, suited for use with the cartridge assembly of FIG. 4, showing the lancing device in an opened position revealing the advancer mechanism of FIG. 6 situated therein, and showing the spring-loaded cam-driven plunger extending through the upper shell of the advancer mechanism.
Figure 8:
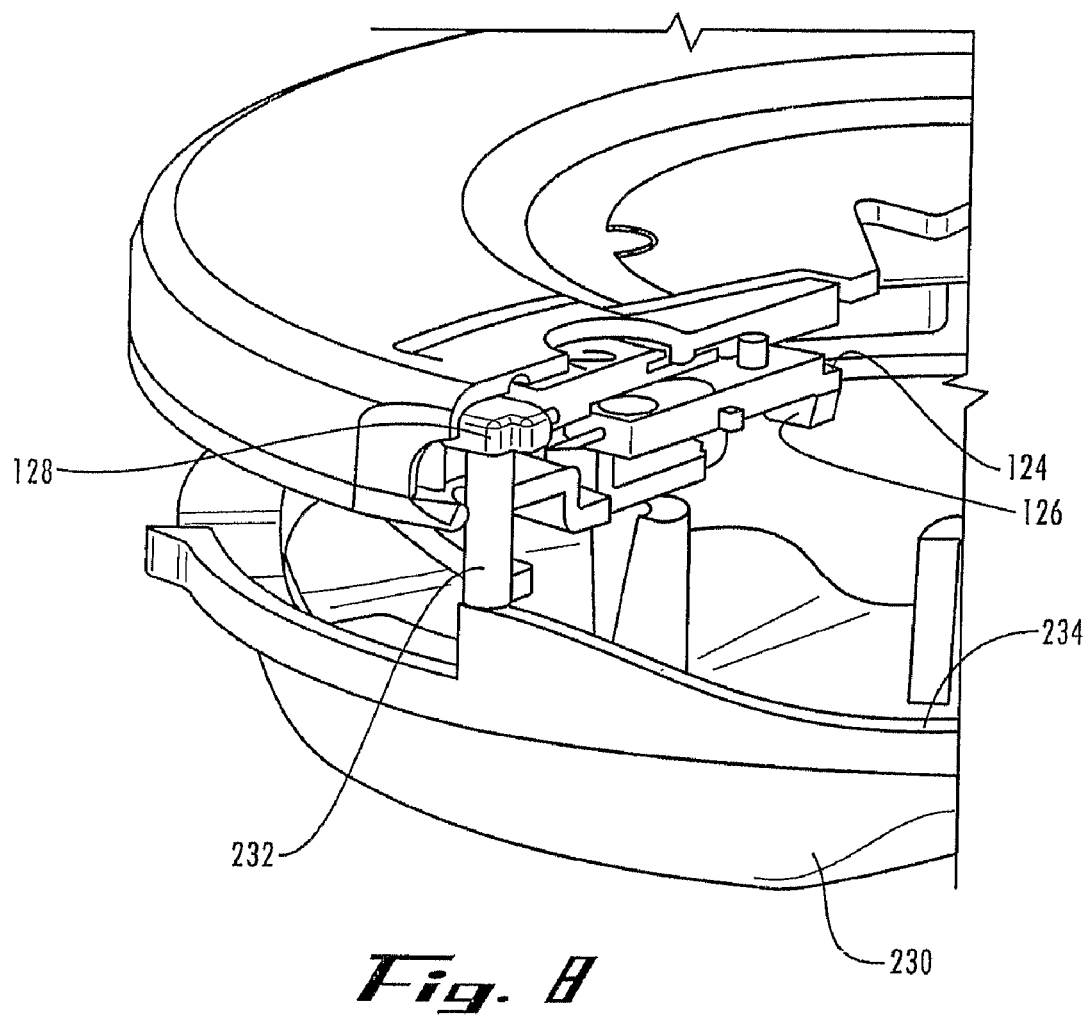
FIG. 8 is a partial cutaway perspective view of the advancer mechanism of FIG. 6, showing the spring-biased cam-driven plunger displacing a cap of an active-position lancet.
Figure 4:
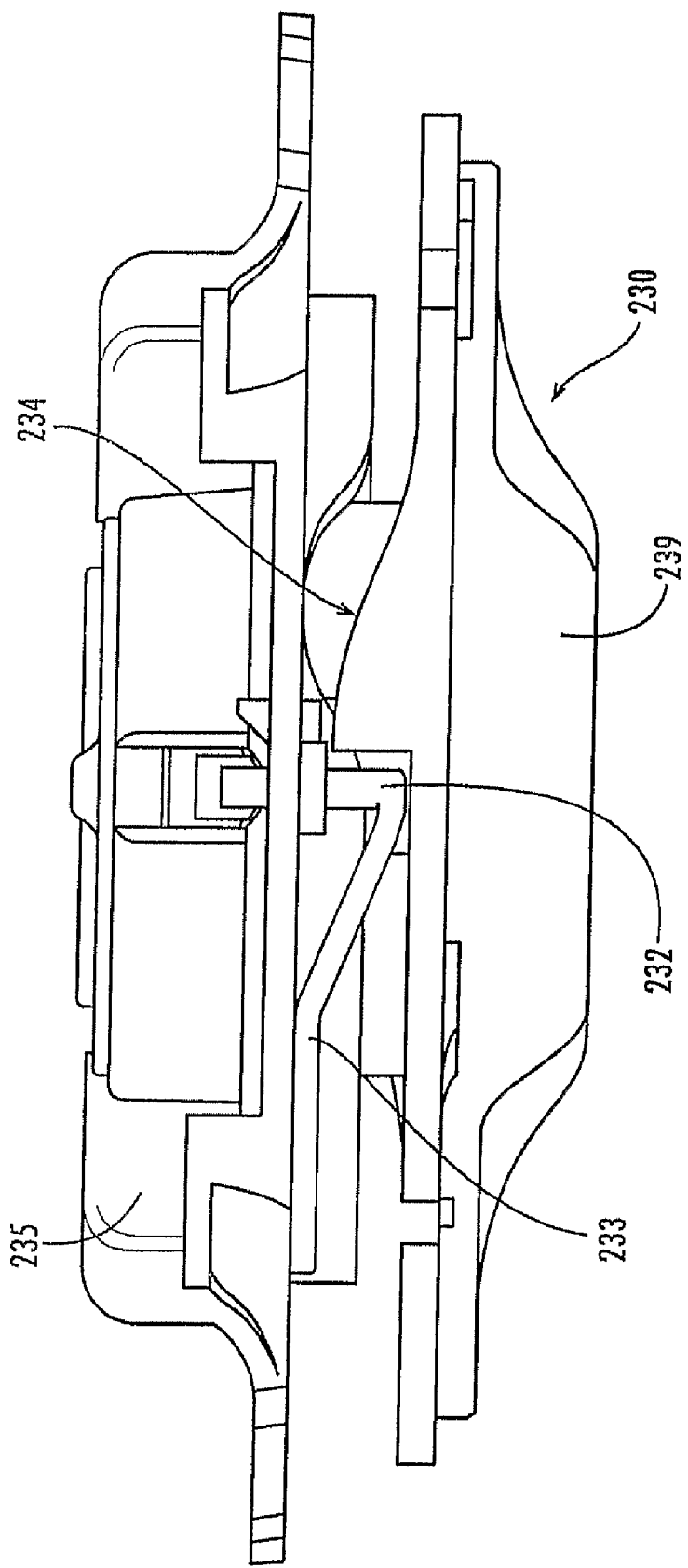
Figure 12:
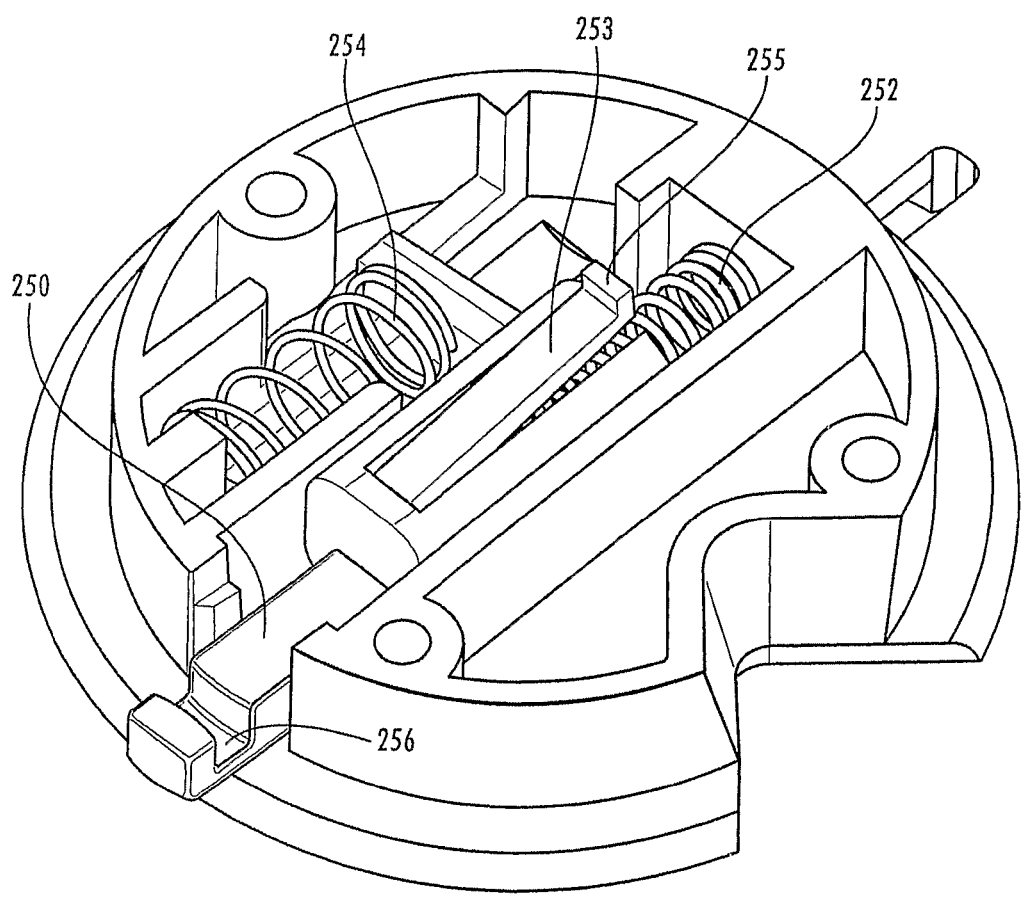
FIG. 12 is a perspective view of a drive and return mechanism of the lancing device of FIG. 7.

The lancing device preferably further comprises a drive mechanism, seen best with reference to FIGS. 7, 12, and 16. The drive mechanism preferably includes a reciprocating plunger 250 that engages the active lancet 20 and drives it radially along its lancing stroke upon activation or firing of the device, through an advanced position where the lancet tip punctures the subject's skin, and back to a retracted position where the lancet tip is shielded within the cartridge. The plunger 250 preferably comprises a recess forming a jaw 256 for receiving and engaging the foot 26 of the active lancet. In a preferred embodiment, two springs, a drive spring 252 and a return spring 254, operate in tandem to drive and return the plunger 250 upon activation of the lancing device by pressing the activating button 220. The springs can be, for example, coil springs, leaf springs, torsion springs, spiral springs, or the like, including other biasing mechanisms. The drive spring 252 is the stronger of the two springs, and drives the active lancet from its initial position into its extended position. The return spring 254 serves to retract the active lancet after lancing the skin. One or more limit members, such as posts or lugs optionally interact with one or both springs, and/or with other portion(s) of the drive mechanism, to more precisely define the equilibrium, retracted, and/or extended position(s) of the plunger. Because the jaw 256 of the plunger is open to the top, it securely but releasably engages the foot 26 of the active lancet to drive the lancet along its lancing stroke, yet allows the cartridge to be removed and replaced at any point during its use. The plunger 250 preferably further comprises a flexible release arm 253 having a catch portion 255 that retains the plunger in its armed state, with drive spring 252 energized prior to activation, and is released by the activating button upon actuation to propel the active lancet through its lancing stroke.

Figure 13:
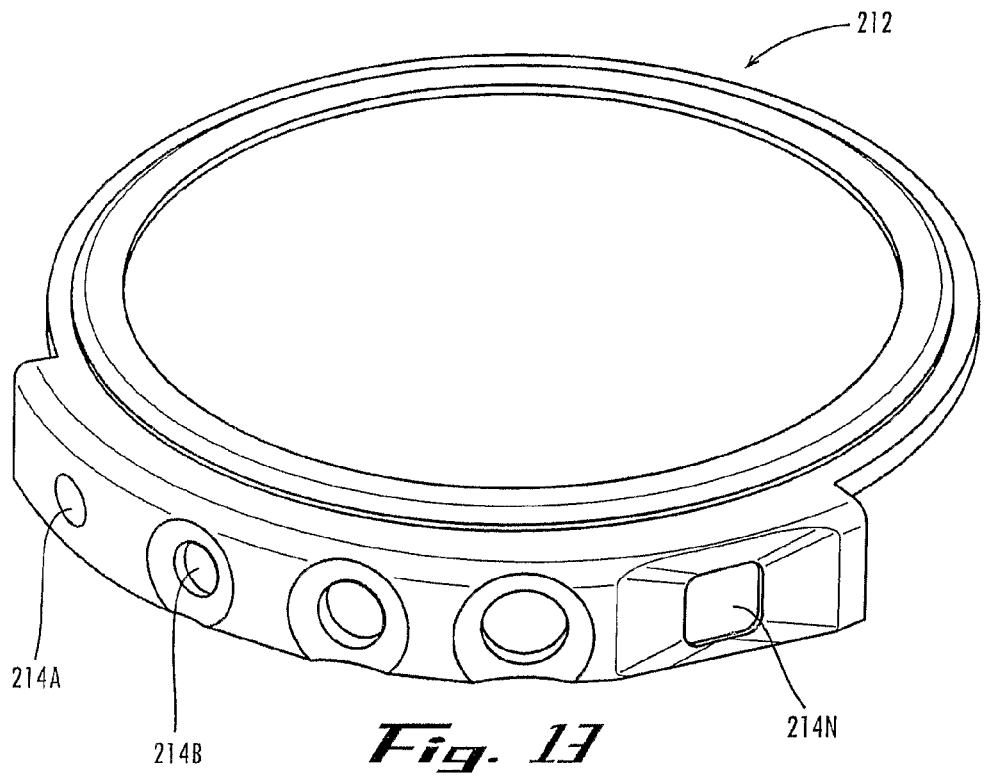
FIG. 13 is a perspective view of a lancing depth adjustment ring of the lancing device of FIG. 7.

The lancing device preferably further comprises a mechanism for depth control, in one embodiment a depth-control ring 212, shown in detail by FIG. 13. The depth ring 212 is positioned near the perimeter of the housing 202 of the lancing device 204, and generally follows the contour of the housing of the lancing device 200. The depth ring 212 defines a plurality of openings 214A, 214B . . . 214N (collectively, the "openings 214") therethrough, through which the tip of a lancet 20 is driven to pierce a skin surface of the subject to obtain a sample of blood. The openings 214 vary in diameter and/or in the depth to which their outer contact surfaces are recessed or countersunk. The depth ring 212 is rotated by the user to selectively position a particular opening 214 in alignment with the puncture position 208, thereby controlling the depth of penetration of the lancet tip into the subject's skin. Because the openings can vary in diameter and in recess depth, the depth ring 212 provides a wide range of depth control. The travel of the lancet 20 preferably is not affected by variation of the position of the depth ring 212, and so the lancing stroke preferably remains uniform regardless of the depth control position.

Figure 14:
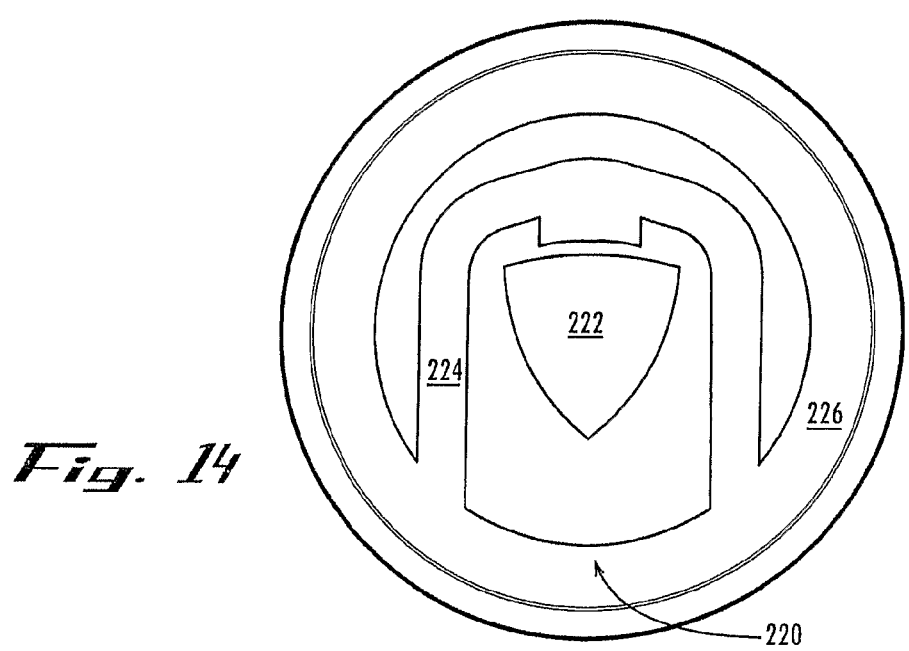
FIG. 14 is a top view of an actuator button portion of the lancing device of FIG. 7.
Figure 15A:
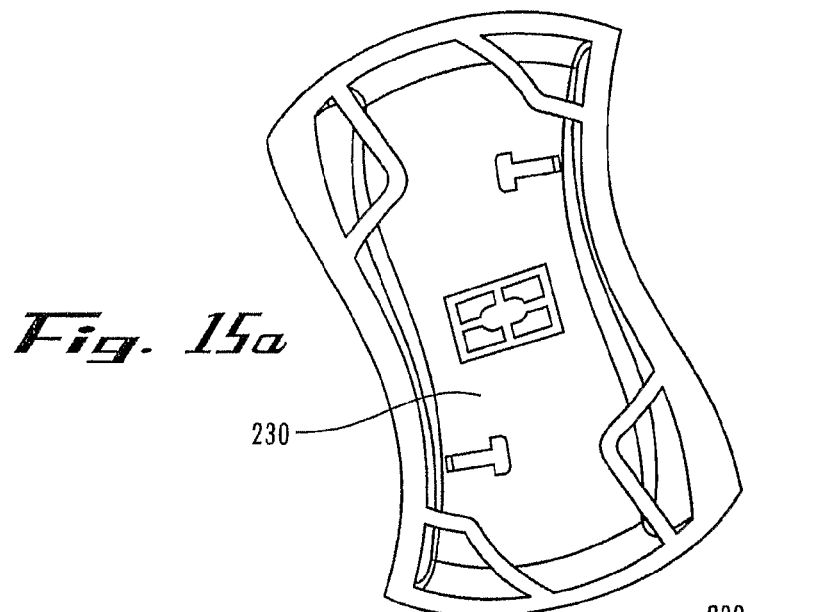
FIG. 15a is a detailed plan view of a portion of the advancer mechanism of FIG. 6 located on the bottom of the housing of the lancing device of FIG. 7.
Figure 15B:
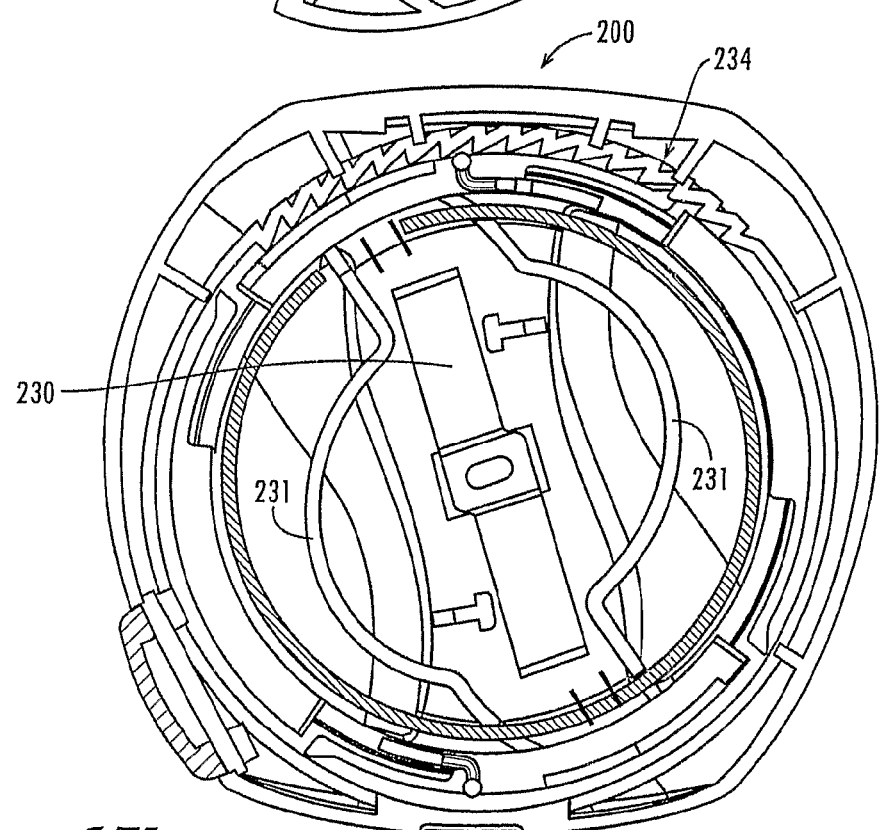

The lancing device preferably further comprises an activating button positioned on the top half-shell 204 of the housing 202 for activating the drive mechanism to propel the active lancet through its lancing stroke. An example configuration of the activating button member 220 is shown in FIG. 14. The activating button member 220 preferably includes a button portion 222, which releases the catch portion 255 of the plunger release arm when pressed by the user to activate or fire the device. The activating button member 220 preferably further comprises one or more integral spring arms 224 for biasing the button 222 outwardly. The activating button member 220 preferably further comprises a retainer ring for securing the depth control ring 212 in place.

The lancing device 200 preferably further comprises an advancer mechanism 230 as seen best with reference to FIGS. 8, 9, 15a, 15b, and 16. In preferred form, the advancer mechanism 230 generally comprises a manually-rotatable element that is operable to advance the carrier to move sequential lancets 20 of a lancet cartridge 118 into the active position. A finger preferably projects from the advancer mechanism 230 through a slot in the bottom housing of the lancet cartridge to engage and advance the lancet carrier through indexed rotational increments corresponding to one lancet position, while the outer housing of the lancet cartridge remains fixed in position. Actuation of the advancer mechanism 230 preferably also functions to engage the active lancet in the jaw of the plunger and retract the plunger to de-cap the active lancet and energize or arm the drive mechanism.

Figure 10:
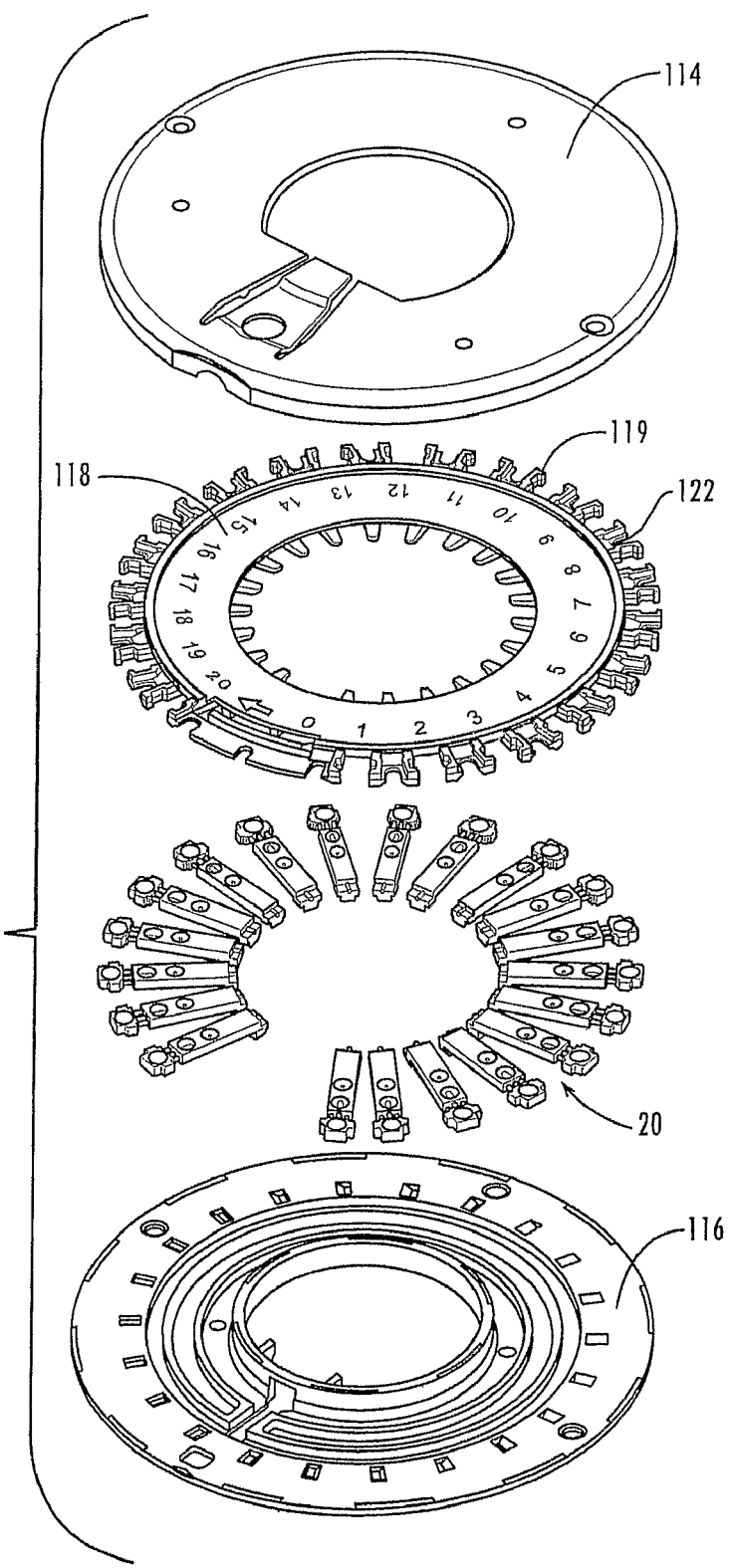
FIG. 10 is another exploded perspective view of the cartridge assembly of FIG. 4.
Figure 11:
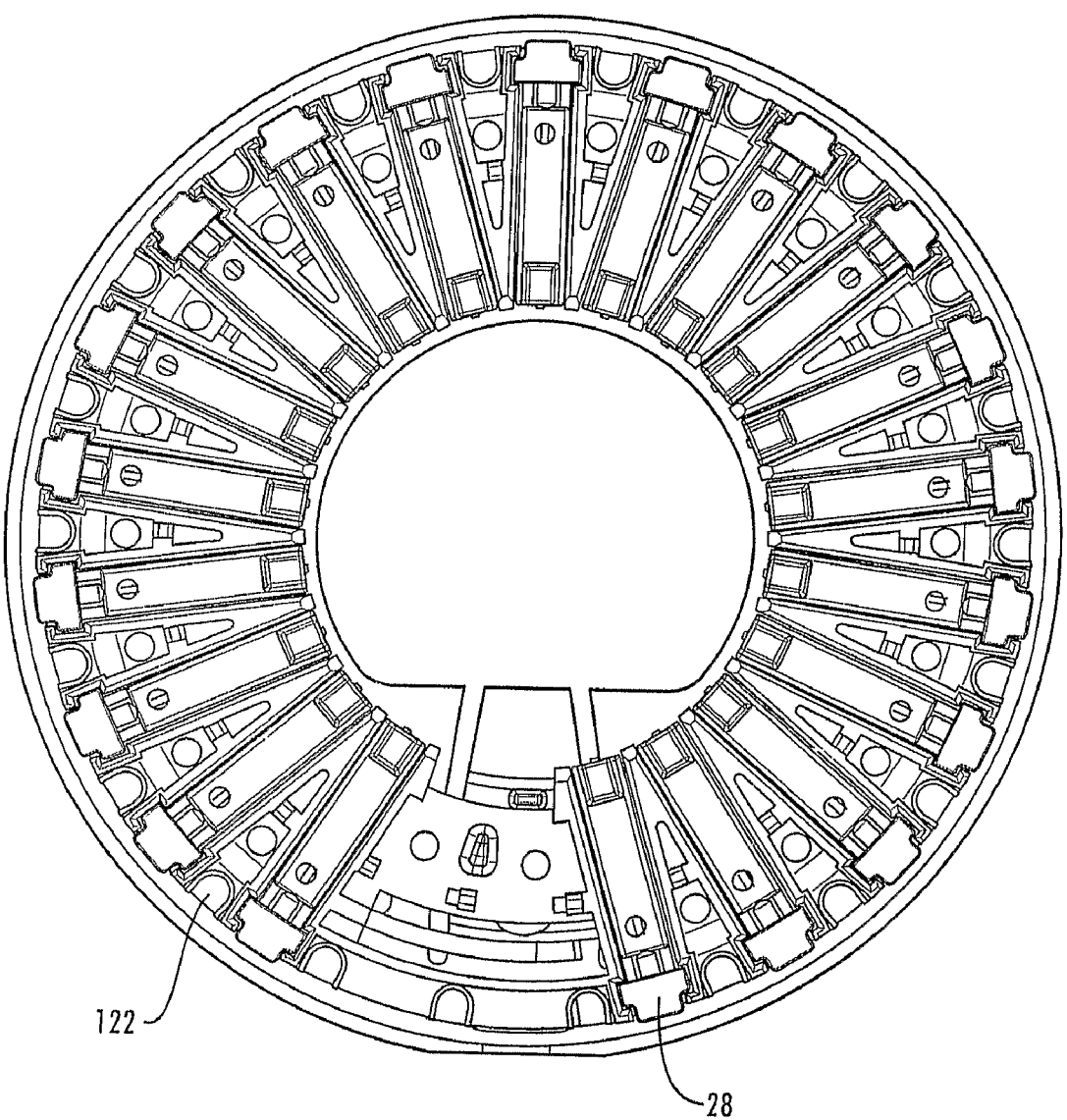
FIG. 11 is a bottom view of the cartridge assembly of FIG. 10 with the bottom cover removed for clarity.

Actuation of the advancer mechanism 230 may also serve to drive the spring-biased cam-driven plunger 232, as described above, if implementing the second example embodiment. Preferably, the advancer mechanism 230 is operable to rotate in one direction only and in discrete increments (e.g., 180° increments). Guide channels or ribs 231 formed in or on the inner face of the advancer mechanism act as cam paths to engage a cooperating follower element of the drive mechanism to retract the drive plunger 250 into its armed state, with drive spring 252 energized. Preferably, the guide channels or ribs 231 are contoured to retract the plunger 250 more slowly at the beginning of the advancing stroke, while the endcap 28 is being detached from the lancet, providing mechanical advantage for smoother and easier operation. A ratchet mechanism 234 may be provided to prevent reverse rotation of the advancer mechanism. Optionally, at the end of the advancing operation, a locating pin is driven upwardly (as by a cam surface similar to the motion of plunger 232 described above) through an opening in the cartridge housing and engaged within a yoke 122 (see FIGS. 10 and 11) between lancet paths on the carrier disk 118, to more precisely position the active lancet and prevent further movement of the carrier disk until the lancing device is fired.

In further preferred embodiments, the carrier 118 comprises a groove 124 that engages a pin on the bottom portion of the housing of the cartridge assembly when all the lancets have been used. This groove and pin combination prevents the cartridge 100 from being moved in either direction after all of the lancets have been used, and thereby prevent a reuse of a non-sterile lancet.

3. Method of Operation

In operation, the user preferably releases a latch 216 to open the lancing device 200. The user then places a preassembled multi-lancet cartridge 100 into the lancing device 200 and closes and latches the housing 202. The user turns the advancer mechanism 230 through a 180° stroke. During the 180° rotation, the carrier 118 is indexed by one lancet position, thus indexing an unused lancet 20 into the active position. The plunger 250 engages foot 26 of the lancet and pulls the lancet radially inwardly. This step energizes the drive spring of the drive mechanism. The catch 255 of the plunger engages a cooperating surface feature of the housing, and the lancet is now in the energized or armed position.

As the lancet 20 is retracted radially inward to charge the drive spring, the cap 28 is held and prevented from moving radially inward with the lancet by the guide track (e.g., detents, fingers, or barbs) 119. In this way, the lancet cap 28 is separated from the lancet body 24. Then the cap displacement mechanism then moves the disengaged cap out of the travel path of the active lancet. In the first example embodiment, the spring arm 50 engages and moves the detached cap 28 out of the lancing stroke path where the cap is held by the guide track, and then the spring element returns to its reset or rest position clear of the lancing stroke. In the second example embodiment, the spring-biased cam-driven plunger 232 engages and moves the detached cap 28 out of the path of travel of the active lancet, then clears the cam and is biased back to its rest or reset position. The guide track (e.g., detents, fingers, or barbs) 119 capture the cap 28 and hold it above the path the lancet 20 will travel in the lancing stroke.

The user may adjust the depth ring 212 to the desired setting to vary the penetration depth. If present, the position lock pin is raised into engagement with the yoke 122 of the cartridge 118 to prevent further movement of the cartridge until activated or fired to release the active lancet to traverse its lancing stroke.

The lancing device 200 is positioned against a finger or other part of the subject's body. The activation button 220 is pressed, releasing the catch 255 of the plunger and allowing the drive spring 252 to drive the plunger 250 and the active lancet engaged in the jaw thereof along a controlled radial path, through an extended position where the lancet tip punctures the subject's skin at the lancing site. The lancet is preferably guided throughout its lancing stroke along three sides by the guide channels of the carrier 118 and on the fourth side by the cartridge housing. Upon reaching the extended position of the lancing stroke, the return spring 254 is energized to bias the plunger 250 and retract the lancet inwardly to a retracted position within the lancet cartridge.

Additional details of the various aspects of the present invention are disclosed in U.S. patent application Ser. No. 11/107,984, filed Apr. 15, 2005; U.S. Provisional Patent Application No. 60/562,712, filed Apr. 16, 2004; and International Application No. PCT/US03/05159 (International Publication No. WO 03/071940 A1), filed Feb. 20, 2003. The content of these patent documents is hereby incorporated herein by reference in its entirety.

4. Linear-Pull Advancing Mechanism

FIGS. 17-53 show a lancing device 300 according to a third example embodiment of the invention. In this embodiment, a linear-pull advancer mechanism 360 replaces the rotational cam drive advancing mechanism 230 and the cap displacement mechanisms previously described. The remainder of the lancing device 300 (including the reusable housing, drive mechanism, and activation mechanism, and the replaceable multi-lancet cartridge) may remain substantially the same as in the first and second example embodiments.

FIGS. 17-20 show details of the construction and operational positioning of the linear-pull advancer mechanism 360. The linear-pull advancer mechanism 360 includes a slider member 362 that is translationally mounted in the base 306 of the clamshell housing 302. The linear-pull slider 362 is preferably an integral piece of molded of plastic, though other materials and fabrication techniques can be used and the individual components can be separated manufactured and assembled together. The linear-pull slider 362 is pulled/extended out and pushed/retracted in through an opening in the housing 302 between a first/retracted position and a second/extended position. This single action operates an indexing ratchet mechanism 363, a cam-guided charger mechanism 365, and a cam-guided lancet cap displacement mechanism 366. In an alternative embodiment, the slider has a laterally extending lever that is slid back-and-forth, a laterally extending knob that is rotated, or another actuating member that is otherwise controlled in a single action to move the slider between its first and second positions to operate the advancer mechanism.

Figure 17:
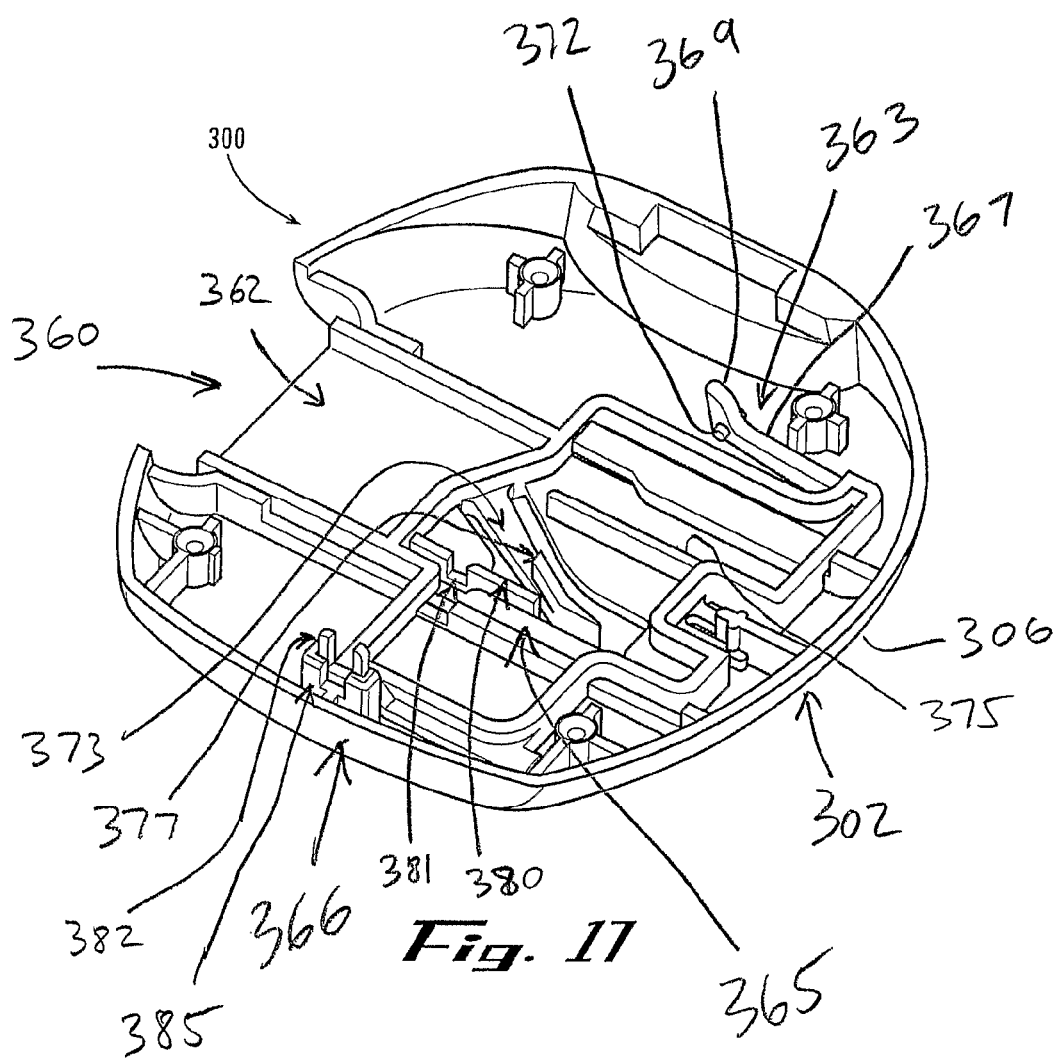
FIG. 17 is a perspective view of a portion of a lancing device in accordance with a third example embodiment of the present invention, showing a linear-pull slider of an advancer mechanism in a retracted position in the bottom portion of the clam-shell housing.
Figure 18:
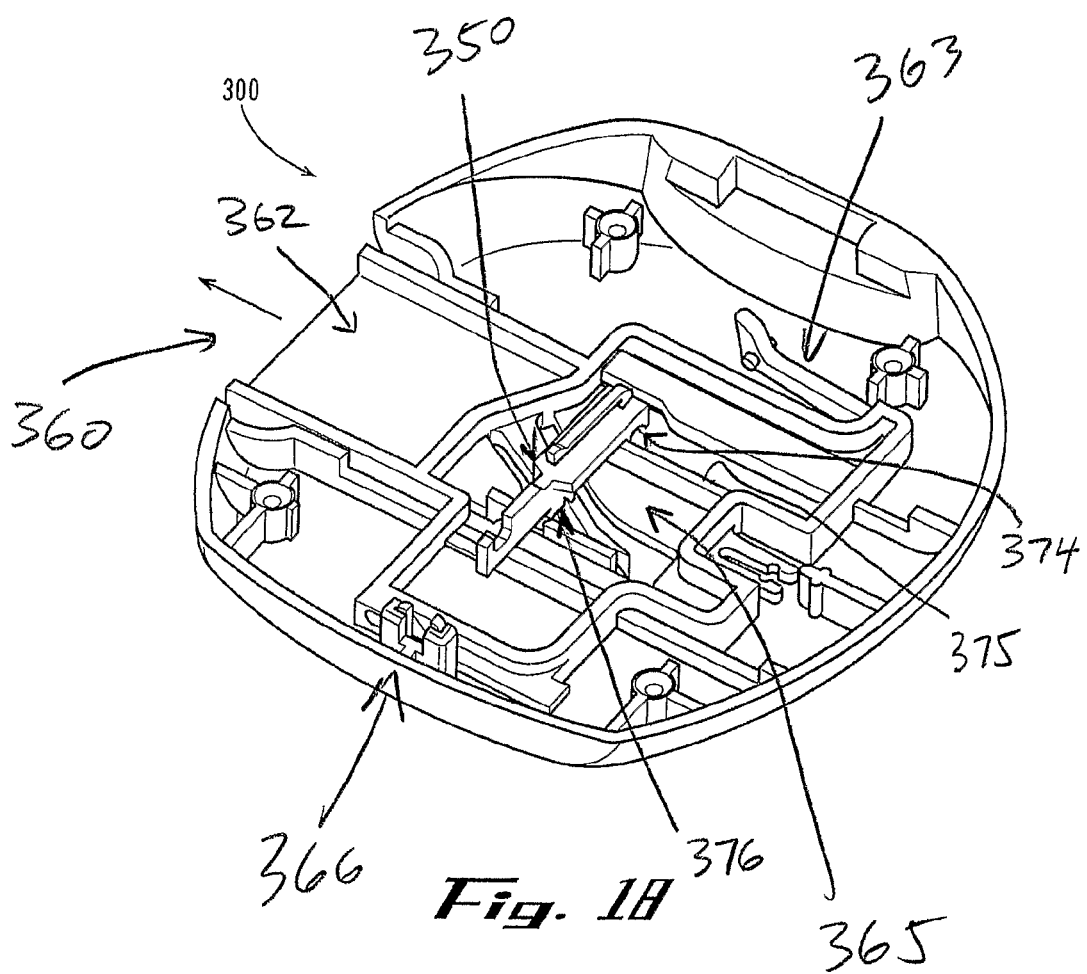
FIG. 18 is a perspective view of the lancing device portion of FIG. 17, showing the slider being pulled from the housing.
Figure 19:
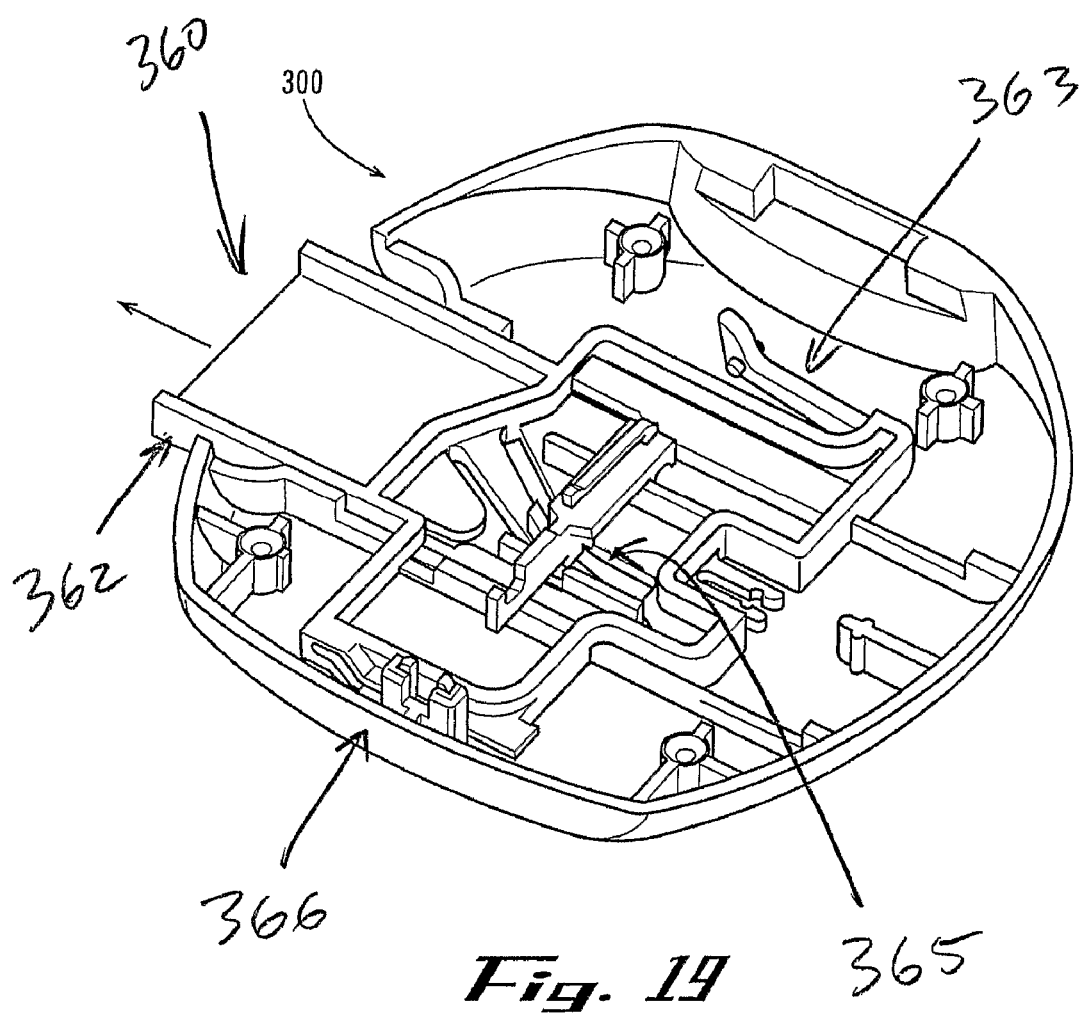
FIG. 19 is a perspective view of the lancing device portion of FIG. 17, showing the slider being pulled further from the housing.
Figure 20:
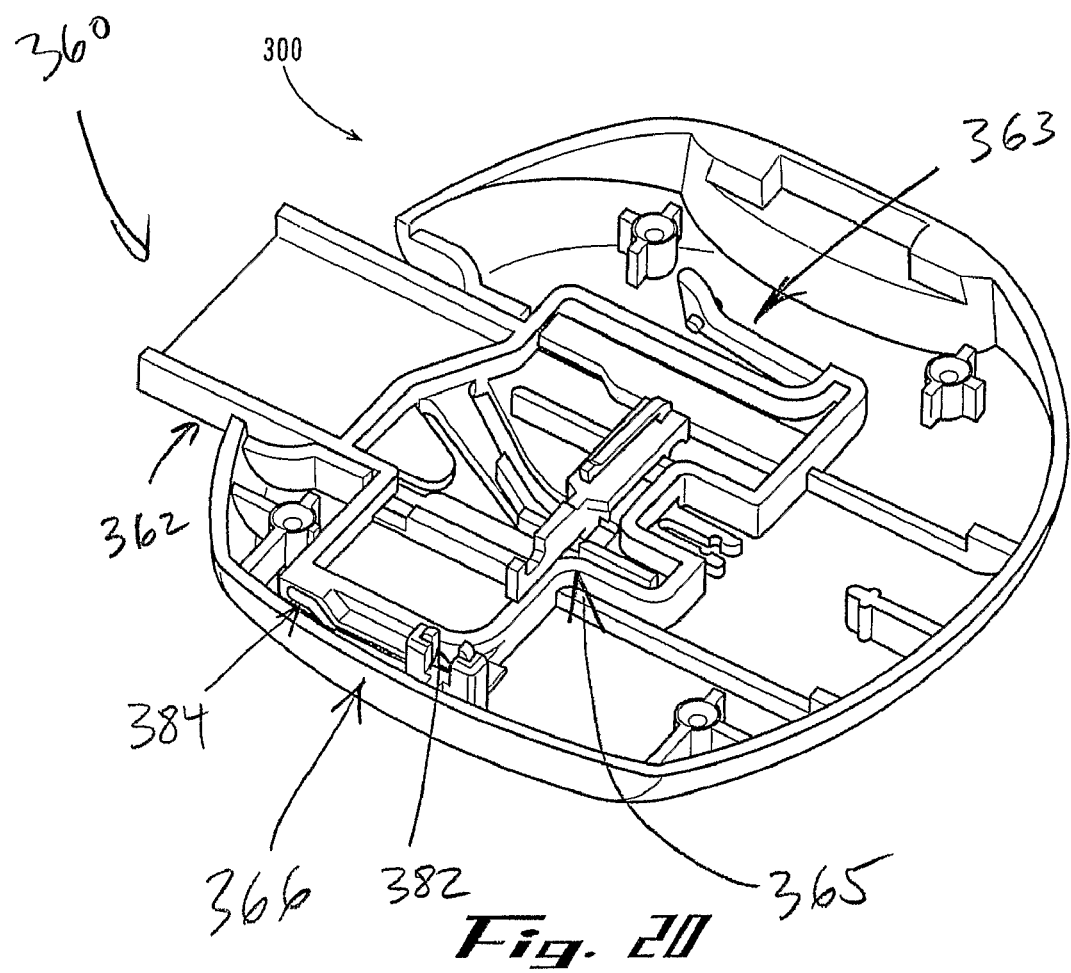
FIG. 20 is a perspective view of the lancing device portion of FIG. 17, showing the slider pulled to an extended position.
Figure 21:
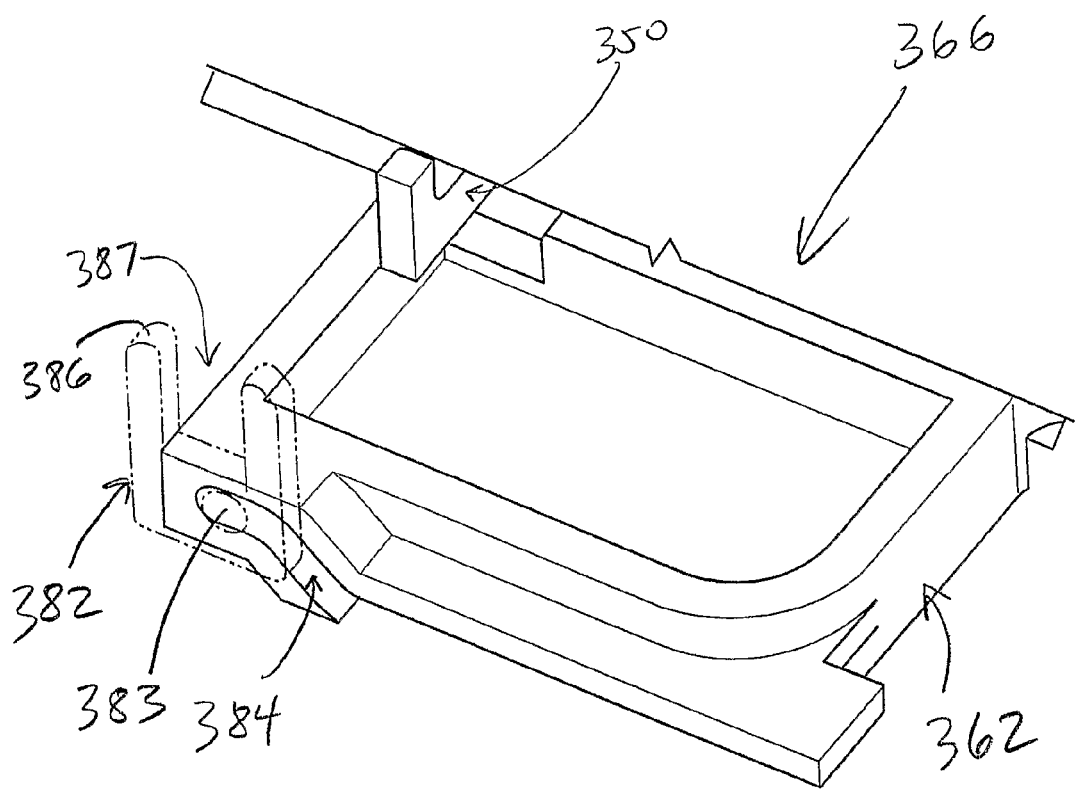
FIG. 21 is a perspective detailed view of part of the lancing device portion of FIG. 17, showing details of a cam-guided cap displacement mechanism.

In FIG. 17, the slider 362 is in its first/fully retracted position relative to the housing 302. In FIG. 18 the slider 362 is partially extended from the housing 302 (for example, about 5 mm), and in FIG. 19 the slider is further extended from the housing (for example, about 10 mm). In FIG. 20, the slider 362 is in its second/fully extended position relative to the housing 302. After the user moves the slider 362 to its fully extended position, the user then moves the slider 362 back to its fully retracted position of FIG. 17. This procedure sequentially advances the lancets in the cartridge to an active position, charges the drive mechanism and separates the cap from the active lancet, and then moves the separated cap from the lancing stroke path of the active lancet. A detent mechanism is preferably provided so that the slider 362 stays in its retracted position until it is pulled out by the user. And cooperating stop surfaces are preferably provided on the slider 362 and the housing base 306 for stopping the slider in its extended position.

Referring to FIGS. 17-20 and 29-30, the indexing ratchet mechanism 363 includes a resilient pawl 367 extending from the slider 362 and a plurality of ratchet teeth 368 for sequentially advancing the lancets in the cartridge to an active position. The pawl 367 is preferably integrally manufactured with the slider 362 and made of molded plastic, though other materials and manufacturing techniques may be used. The materials and dimensions of the pawl 367 are selected so that it is resiliently deflectable. The teeth 368 are pin-like protrusions that extend downward from the lancet carrier 318, and the teeth and the lancets are correlated in a one-to-one ratio. In an alternative embodiment, the teeth 368 are provided by notches in the carrier.

The pawl 367 has a head 369 that extends through a slot 370 in a cover panel 371 that attaches to the base 306 of the housing 302. The cover 371 protects the components of the advancer mechanism under it from damage when replacing lancet cartridges. In addition, the pawl 367 has two (or another number of) laterally extending tabs 372 that prevent the pawl 3667 from being pulled up through the slot 370.

The pawl head 369 engages the teeth 368, which extend downward from the lancet carrier 318 through a circular slot 313 in the cartridge housing 312. Advancing the pawl 367 advances the lancet carrier through indexed rotational increments corresponding to one lancet position, while the outer housing 312 of the lancet cartridge 310 remains fixed in position. In an alternative embodiment, the pawl head extends up into a circular slot in the cartridge and the teeth are defined by the lancets. And in another alternative embodiment, the teeth extend from the cartridge housing so that the entire cartridge is rotated. The cartridge housing 312 and the cover 371 are shown in FIG. 30 but not in FIGS. 31-37 for simplicity.

Figure 30:
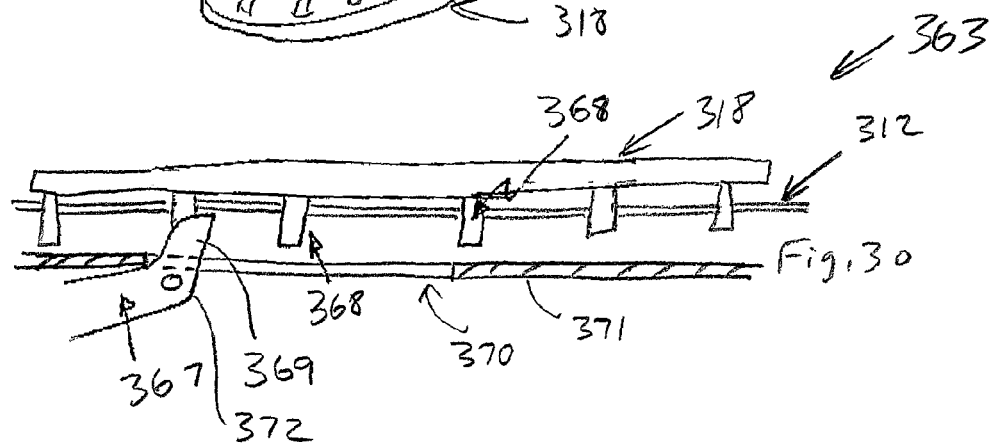
FIG. 30 is a side view of a portion of the indexing ratchet mechanism of the lancing device of FIG. 17, showing a resilient pawl and the ratchet teeth.
Figure 31:
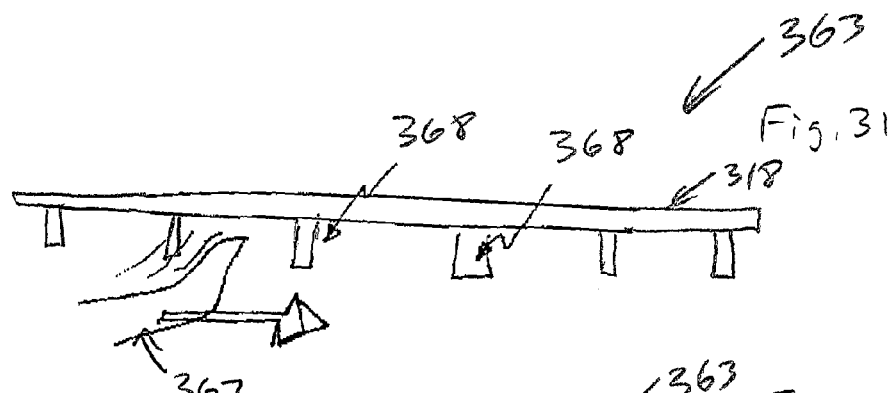
FIG. 31 is a side view of the ratchet mechanism of FIG. 30, showing the pawl being advanced as the slider of FIG. 17 is pulled/extended.
Figure 32:
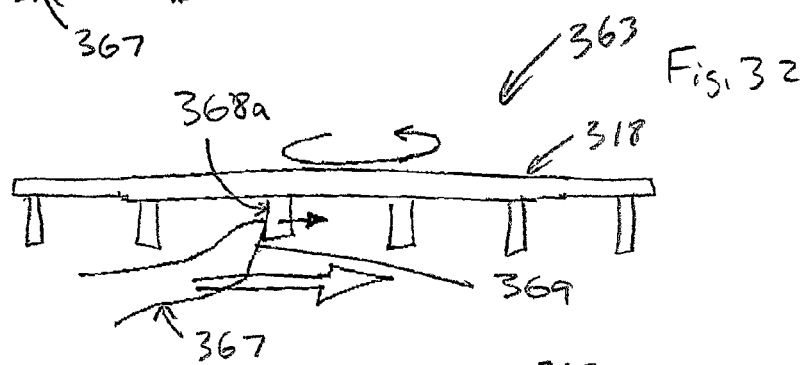
FIG. 32 is a side view of the ratchet mechanism of FIG. 30, showing the pawl further advanced into engagement with one of the teeth.
Figure 33:
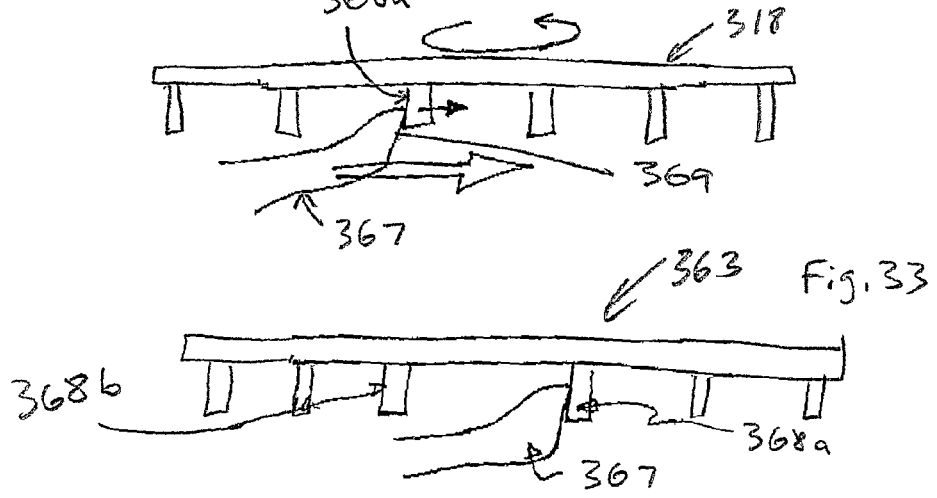
FIG. 33 is a side view of the ratchet mechanism of FIG. 30, showing the pawl fully extended, the engaged tooth advanced, and the lancet carrier rotated/indexed as the slider is moved to the extended position of FIG. 20.
Figure 38:
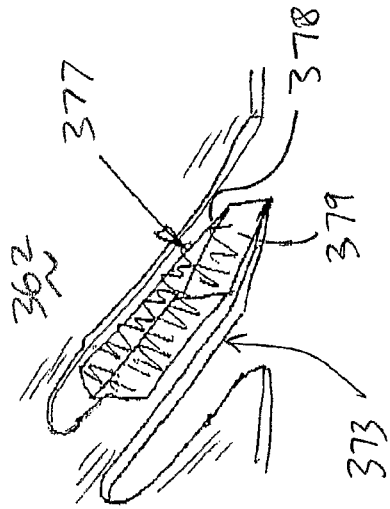
FIG. 38 is a perspective view of a reciprocating plunger of a cam-guided charger mechanism of the advancer mechanism of the lancing device of FIG. 17.
Figure 39:
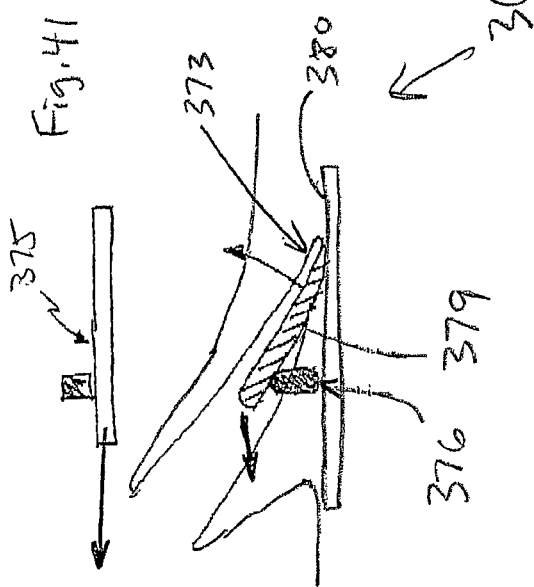
FIG. 39 is a perspective view of a deflectable cam arm of the cam-guided charger mechanism of the advancer mechanism of the lancing device of FIG. 17.

FIGS. 30-37 show details of the operation of the indexing ratchet mechanism 363 of the advancer mechanism 360. FIG. 30 shows the position of the pawl 367 and the ratchet teeth 368 when the slider 362 is in its retracted position of FIG. 17. In FIG. 31, the pawl 367 is being advanced (as indicated by the directional arrow) as the slider 362 is pulled/extended. In FIG. 32, the pawl 367 is advanced until a pushing surface of the pawl head 369 engages a first one of the teeth 368a. Linearly advancing the pawl 367 (as indicated by the linear directional arrow) rotationally advances the lancet carrier 318 (as indicated by the rotational directional arrow). The positions shown in FIGS. 31 and 32 correspond to the slider positions shown in FIGS. 18 and 19, respectively. In FIG. 33, the pawl 367 is fully extended, the engaged first tooth 368a advanced, and the lancet carrier 318 rotated/indexed to move the next lancet to the active position for use. In this position, the slider 362 is in the extended position of FIG. 20.

In FIG. 34, the pawl 367 is being retracted (as indicated by the directional arrow) as the slider 362 is pushed/retracted. In FIG. 35, the pawl 367 is further retracted until an angled deflection surface of the pawl head 369 engages a second one of the teeth 368b, which causes the pawl to resiliently deflect under the second tooth (as indicated by the directional arrows). The lancing device 300 has conventional cooperating ratchet features to prevent reverse rotation of the carrier 318. And in FIG. 36, the pawl 367 is fully retracted, the lancet corresponding to the first tooth 368a is ready to be used, and the second tooth 368b is ready to next be engaged to incrementally advance the carrier again. In this position, the slider 362 is back in the retracted position of FIG. 17, ready for use to advance the second tooth 368b. In this way, the lancing device 300 cycles used lancets back onto the carrier 318 so that there are no loose lancets in the cartridge.

FIG. 37 shows an empty position 368x in the series of teeth where there is no tooth on the carrier 318. The empty position 368x is between the last tooth 368n and the first tooth 368a. Because there is no indexing tooth in the empty position 368x, the carrier 318 cannot be advanced further after all of the lancets in the cartridge have been used. In this position, the lancing device 300 is locked and safe.

Referring to FIGS. 17-20 and 38-39, the cam-guided charger mechanism 365 includes a reciprocating plunger or piston 350 and a resiliently deflectable cam arm 373. The plunger 350 is translationally mounted on the slider 362 and is driven by the drive spring to propel the active lancet through its lancing stroke. Preferably, the plunger 350 comprises a recess forming a jaw 356 for receiving and engaging a foot or other part of the active lancet. The plunger 350 preferably further comprises a flexible release arm 353 having a catch portion 355 that retains the plunger in its armed state, with the drive spring energized prior to activation, and is released by actuating the activating button to propel the active lancet through its lancing stroke. In addition, a locking follower 374 extends from the plunger 350 (i.e., downward from the bottom of the plunger) for engagement with an upstanding locking wall 375 defined by the slider 362. And a charging follower 376 extends the plunger 350 (i.e., downward from the bottom of the plunger and spaced apart from the locking follower 374).

The resiliently deflectable cam arm 373 is preferably integrally manufactured with the slider 362 and made of molded plastic, though other materials and manufacturing techniques may be used. The materials and dimensions of the cam arm 373 are selected so that it is resiliently deflectable. In addition, the arm 373 has a cantilevered member 377 defining a charging cam surface 378 and a deflecting cam surface 379. The deflecting cam surface 379 engages the plunger charging follower 376 to deflect the cam arm 373. And the charging cam surface 378 engages and guides the plunger charging follower 376 to retract the plunger 350 and energize the drive spring.

Furthermore, a wall 380 extends upward from the housing base 306 and remains stationary as the slider 362 is moved through its extending/retracting stroke. The wall 380 has an opening 381 for the plunger charging follower 376 to pass through when the lancet is propelled through its lancing stroke.

Figure 40:
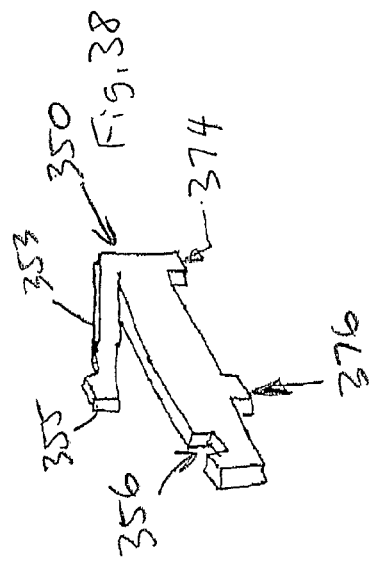
FIG. 40 is a plan view of a portion of the cam-guided charger mechanism of FIGS. 38 and 39, showing the cam arm and a charging follower of the plunger when the slider is in its retracted position of FIG. 17.
Figure 41:
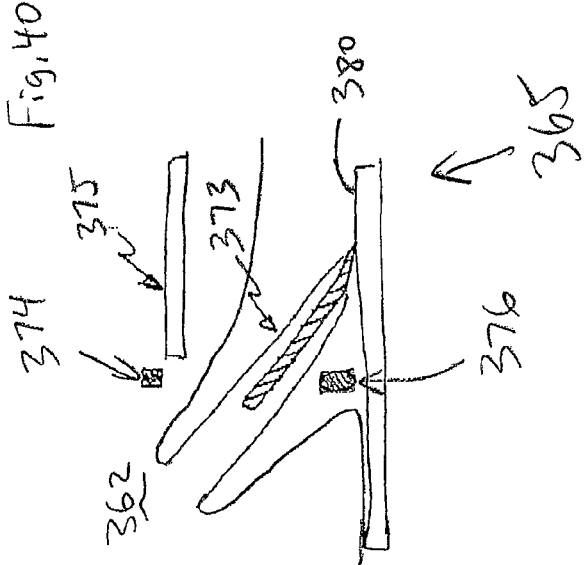
FIG. 41 is a plan view of the cam-guided charger mechanism of FIG. 40, showing the cam arm being resiliently deflected by the charging follower of the plunger as the slider is pulled/extended.
Figure 42:
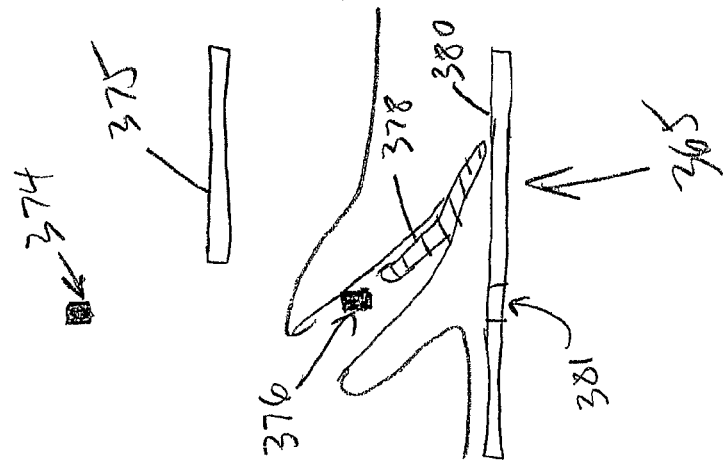
FIG. 42 is a plan view of the cam-guided charger mechanism of FIG. 40, showing the cam arm returned to its neutral position after moving past the charging follower, as the slider is moved to its fully extended position of FIG. 20.

FIGS. 40-44 show details of the operation of the cam-guided charger mechanism 365 of the advancer mechanism 360. FIG. 40 shows the position of the cam arm 373 and the charging follower 376 of the plunger 350 when the slider 362 is in its retracted position of FIG. 17. The followers 374 and 376 of the plunger 350 are shown in this series of figures, but not the body of the plunger, for clarity. In FIG. 41, the slider 362 is being pulled/extended (as indicated by the linear directional arrows) so that the deflecting cam surface 379 comes into engagement with the plunger charging follower 376, which deflects the cam arm 373 (as indicated by the curved directional arrow). The followers 374 and 376 and the plunger 350 remain stationary as they do not move in the stroke direction of the slider 362. In FIG. 42, the slider 362 has been moved to its fully extended position of FIG. 20, and the deflecting cam surface 379 has been moved laterally past the charging follower 376 so that the cam arm 373 has resiliently returned to its neutral position adjacent the wall 380.

Figure 43:
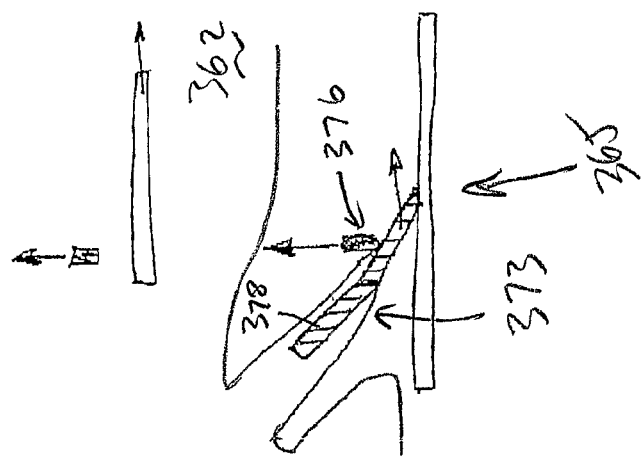
FIG. 43 is a plan view of the cam-guided charger mechanism of FIG. 40, showing the cam arm driving backward the charging follower to charge the drive mechanism as the slider is pushed/retracted.
Figure 44:
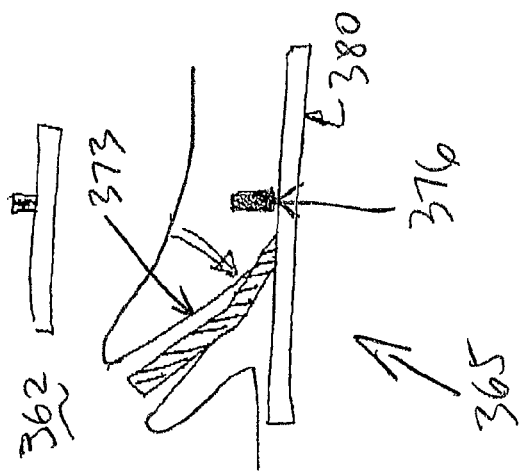
FIG. 44 is a plan view of the cam-guided charger mechanism of FIG. 40, showing the charging follower driven back until the plunger is retained in its charged position as the slider is moved to its fully retracted position of FIG. 17.

In FIG. 43, the slider 362 is being pushed/retracted back in (as indicated by the directional arrows) so that the charging cam surface 378 now comes into engagement with the plunger charging follower 376. The cam arm 373 is positioned adjacent the wall 380 with no gap for the charging follower 376 to slip or pry through, and the cam member 377 is angled to prevent its deflection when encountering the charging follower from this direction. In this way, the cam arm 373 functions as a one-way valve for positioning the charging follower 376 so that it can be driven by the charging cam surface 378. The charging cam surface 378 then drives backward the charging follower 376 (as indicated by the directional arrow) and thus the plunger 350 to charge the drive mechanism as the slider is pushed/retracted. In FIG. 44, the slider 362 is pushed/retracted back to its fully retracted position of FIG. 17. In this position, the charging cam surface 378 has driven back the plunger 350 to its armed position, and the release arm catch 355 of the plunger 350 has been engaged to retain the plunger in this armed position.

The carrier 318 includes cap guide tracks similar to the cap guide tracks 19 of the first embodiment. The cap guide tracks hold the lancet caps in place so that, when the active lancet is retracted by the plunger 350, the active lancet is separated from its cap. In addition, the cap guide tracks guide the lancet caps when they are transversely displaced out of the lancing travel path, as described with respect to the cam-guided cap displacement mechanism 366.

The plunger 350 then can be released from its armed position to propel the active lancet through its lancing stroke by operation of the activating button. In the position shown in FIG. 44, the locking wall 375 that extends upward from the slider 362 has been moved laterally from a blocking position in the path of the locking follower 374 of the plunger 350. And the charging follower 376 remains aligned with the opening 381 in the stationary wall 380. So there are no obstructions in the travel path of the plunger 350, and it is ready to be activated. After the lancing device 300 is activated to lance the subject's skin, the cam-guided charger mechanism 365 of the advancer mechanism 360 is again in the position shown in FIG. 40.

Referring to FIGS. 17-21 and 45-46, the cam-guided cap displacement mechanism 366 includes a lifter member 382 with a follower 383 that rides along a cam surface 384 for transversely moving the separated lancet cap out of the lancing stroke path of the active lancet. The lifter 382 moves transversely to the lancing travel path and is guided by a lifter guide track 385. In addition, the lifter 384 is preferably fork-shaped, with two (or another number of) tines having displacing surfaces 386 and an opening 387 through which the lancet body passes when traveling to its puncturing position. The cam surface 384 is preferably formed at least in part by a slot defined in the slider 362, with a raising cam surface 384a and a lowering cam surface 384b for positively controlling the position of the lifter 382. In an alternative embodiment, the cam-guided cap displacement mechanism 366 includes only one cam surface for either raising or lowering the lifter, and a spring element for moving the lifter in the other, non-cam-driven, direction.

Figure 50:
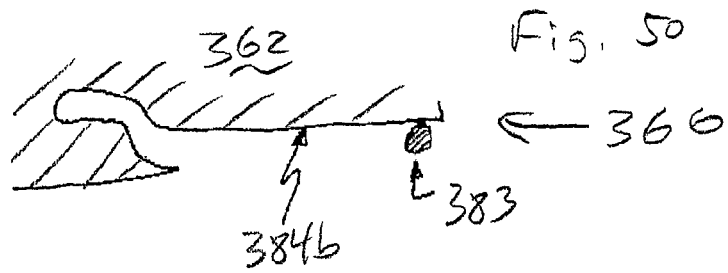
FIG. 50 is a side view of the cam-guided cap displacement mechanism of FIG. 47, showing the lifter follower and the cam surface when the slider is in the fully extended position of FIG. 20.

FIGS. 47-53 show details of the operation of the cam-guided cap displacement mechanism 366 of the advancer mechanism 360. FIG. 47 shows the lifter follower 383 in its raised position due to its engagement with the raising cam surface 384a, when the slider 362 is in its retracted position of FIG. 17. In FIG. 48, the lifter follower 383 is being guided downward along the lowering cam surface 384b as the slider 362 is pulled/extended (as indicated by the directional arrow). In FIG. 49, the lifter follower 383 is lowered and the slider 362 is further pulled/extended laterally past the lifter follower 383. The positions shown in FIGS. 48 and 49 correspond to the slider positions shown in FIGS. 18 and 19, respectively. With the lifter 382 in its lowered position, it is out of the way so that the next lancet can be rotationally advanced to the active position by the indexing ratchet mechanism 363. In order to prevent the lifter 382 from moving lower, the lancing device 300 may be provided with a base for the slider 362 on which the lifter follower 383 rides, a guide surface on the interior wall of the base 306 of the housing 302, and/or a stop surface on the slider 362, the housing 302, the lifter guide track 385, or elsewhere on the lancing device. And FIG. 50 shows the lowered position of the lifter follower 383 relative to the slider 362 when the slider is in the fully extended position of FIG. 20.

Figure 51:
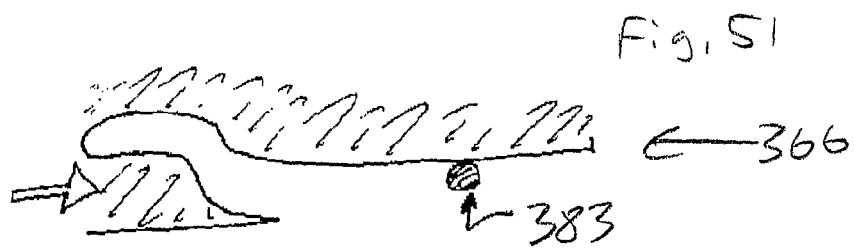
FIG. 51 is a side view of the cam-guided cap displacement mechanism of FIG. 47, showing the lifter follower riding along the cam surface as the slider is pushed/retracted.
Figure 52:
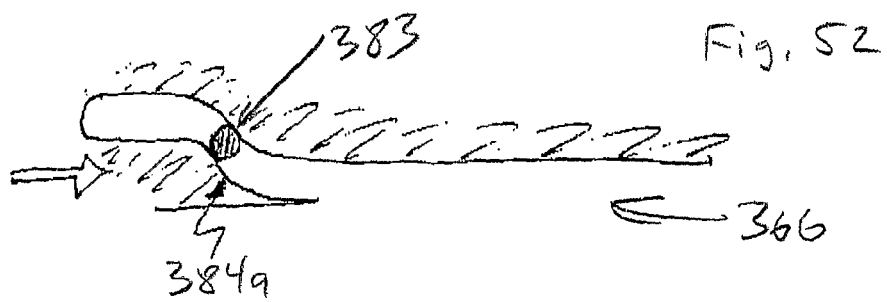
FIG. 52 is a side view of the cam-guided cap displacement mechanism of FIG. 47, showing the lifter follower guided up along the cam surface as the slider is pushed/retracted further.
Figure 53:
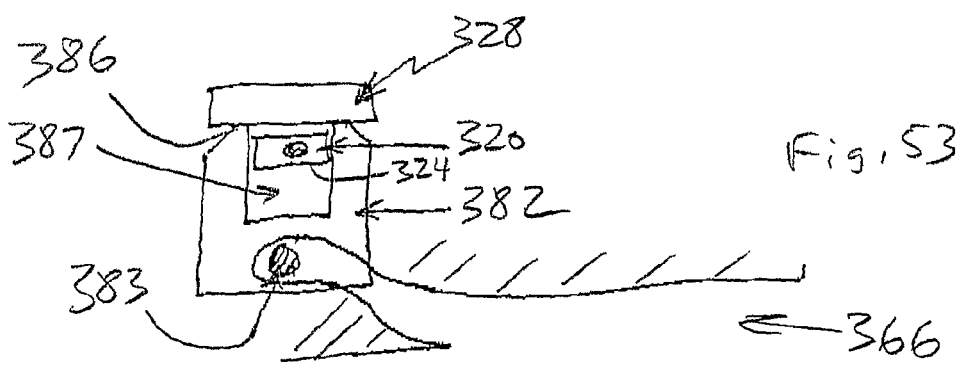
FIG. 53 is a side view of the cam-guided cap displacement mechanism of FIG. 47, showing the lifter raised by the follower-cam engagement to displace the lancet cap when the slider is in its retracted position of FIG. 17.

In FIG. 51, the slider 362 is being pushed/retracted back in (as indicated by the directional arrow) laterally past the lowered lifter follower 383. The lifter 382 remains lowered during this first part of the slider retraction motion, while the lancet cap 328 is being separated from the lancet body 324 by operation of the cam-guided charger mechanism 365. In FIG. 52, the lifter follower 383 is being driven up along the raising cam surface 384a as the slider 362 is pushed/retracted further in the second part of the slider retraction motion. And in FIG. 53, the lifter 382 is returned to its raised position, with the lifter follower 383 driven to its raised position by the raising cam surface 384a as the slider 362 is pushed/retracted back to its fully retracted position of FIG. 17.

As the lifter 382 is raised its displacing surfaces 386 push the now separated lancet cap 328 out of the lancing travel path of the active lancet 320. Preferably, the displaced lancet cap 328 is retained there by features of the cap guide track of the lancet carrier 318. The lancet 320 now can be launched into its lancing stroke, during which it will pass through the opening 387 in the lifter 384 as it travels to its puncturing position. When the lancet 320 passes through the lifter opening 387, this maintains positioning of the active lancet and prevents rotation of the lancet carrier.

Figure 22A:
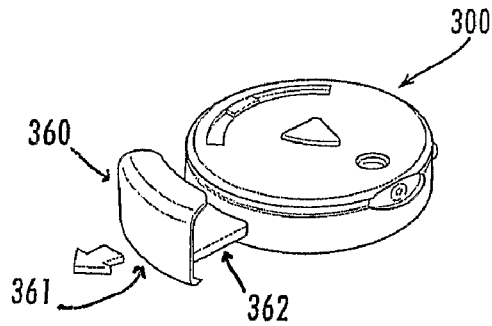
FIG. 22a is a top perspective view of the lancing device of FIG. 17, showing the slider of the advancer mechanism being pulled from the retracted position to the extended position to initiate a process for inserting a new cartridge.
Figure 22D:
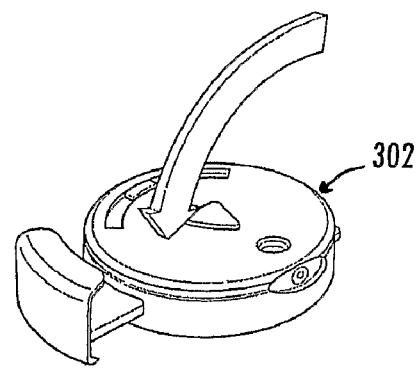
FIG. 22d is a top perspective view of the lancing device of FIG. 22a, showing the housing being closed.
Figure 22B:
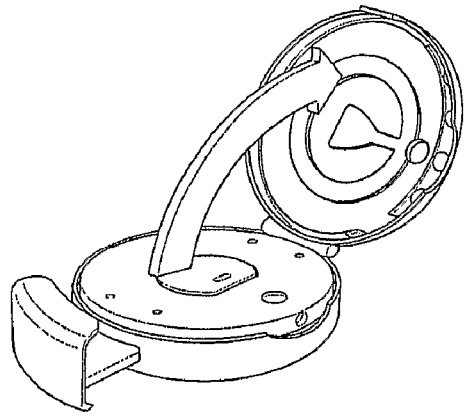
FIG. 22b is a top perspective view of the lancing device of FIG. 22a, showing the housing being opened.
Figure 22E:
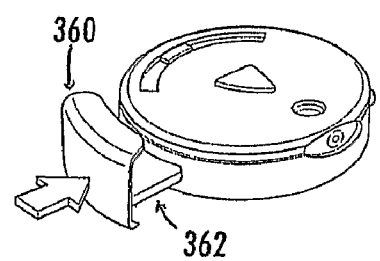
FIG. 22e is a top perspective view of the lancing device of FIG. 22a, showing the slider being pushed back in to its retracted position.
Figure 22C:
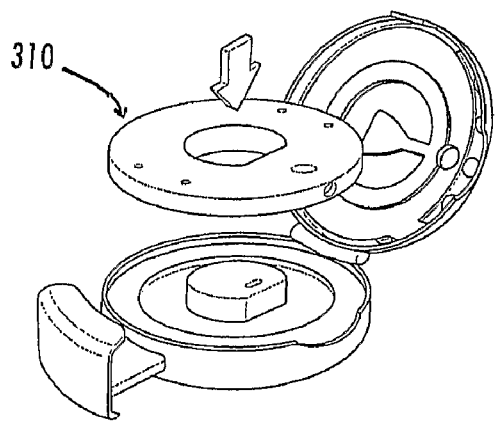
FIG. 22c is a top perspective view of the lancing device of FIG. 22a, showing the cartridge being inserted into the housing.
Figure 22F:
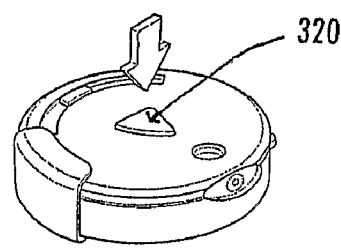
FIG. 22f is a top perspective view of the lancing device of FIG. 22a, showing the activating button being pressed to activate the lancing device for lancing with an initial one of the lancets.

Having described details of the construction, operation, and use of the lancing device 300, we now refer to FIGS. 22a-22f, which illustrate a process for inserting a new lancet cartridge 310 into the housing 302 of the lancing device 300. In FIG. 22a, the slider 362 of the advancer mechanism 360 is being pulled from the first/retracted position to the second/extended position. In FIG. 22b, the housing 302 is being opened. In FIG. 22c, the lancet cartridge 310 is being inserted into the opened housing 302. In FIG. 22d, the housing 302 is being closed. In FIG. 22e, the slider 362 is being pushed back in to its retracted position. The lancing device 300 is now ready for use. In FIG. 22f, the activating button 320 is being pressed to activate the lancing device 300 for lancing with an initial one of the lancets.

Figure 22G:
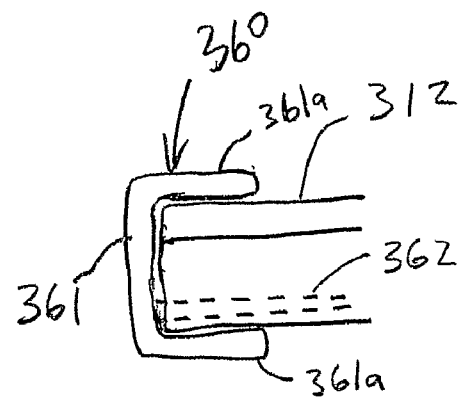
FIG. 22g is a partial side view of the lancing device of FIG. 22a, showing the C-shaped handle that locks the housing closed when the slider is in its retracted position.

As shown in FIG. 22g, the advancer mechanism 360 includes a handle 361 that extends from the slider 362 to push and pull it. The handle 361 is preferably C-shaped with two flanges 361a that wrap around the top and bottom portions of the clamshell housing 302 in a clamp-like fashion. When the advancer mechanism 360 is in the fully retracted position, the flanges 361a of the handle 361 overlap the housing top and bottom portions to lock it closed. This prevents a user from opening the housing 302 when a lancet has been advanced into the active position and the drive member has been charged. This is why the advancing mechanism 360 is pulled out and pushed in as shown in the steps of FIGS. 22a and 22e. The flanges 361a of the handle 361 are long enough that, in order to have the needed clearance to open the housing 302 (i.e., with the flanges 361a not overlapping the housing top and bottom), the handle must be pulled all of the way out. This ensures that the housing 302 cannot be opened until the charged lancet has been advanced from the active position and a next uncharged lancet advanced to the active position.

Figure 23A:
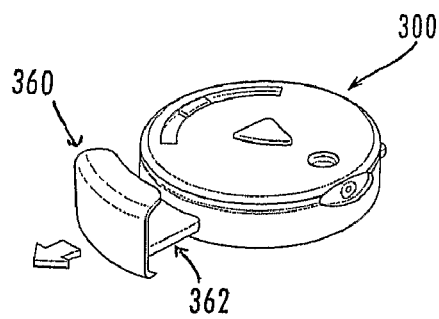
FIG. 23a is a top perspective view of the lancing device of FIG. 17, showing the slider being pulled from the retracted position to the extended position to initiate a process for advancing a next one of the lancets for lancing.
Figure 23B:
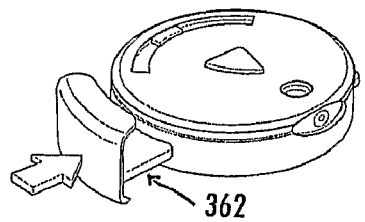
FIG. 23b is a top perspective view of the lancing device of FIG. 23a, showing the slider being pushed back in to its retracted position.
Figure 23C:
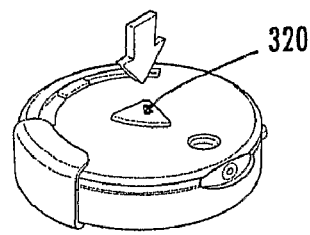
FIG. 23c is a top perspective view of the lancing device of FIG. 23a, showing the activating button being pressed for lancing with the next lancet.

FIGS. 23a-23c illustrate a process for advancing a next one of the lancets for lancing. In FIG. 23a, the slider 362 of the advancer mechanism 360 is being pulled from the retracted position to the extended position to rotate the carrier, which advances the spent lancet out of the active position and advances the next lancet into the active position. In FIG. 23b, the slider 362 is being pushed back in to its retracted position to charge and de-cap the active lancet and then to displace the cap from the lancing stroke path. The lancing device 300 is now ready for activation to lance with the next lancet. And in FIG. 23c, the activating button 320 is being pressed to activate the lancing device 300 for lancing with the next lancet.

Figure 24A:
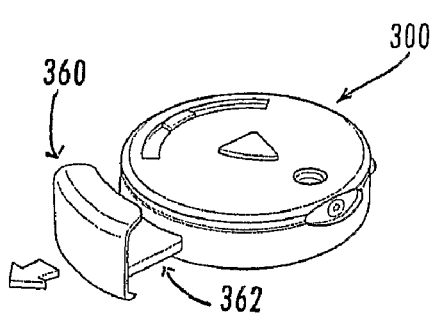
FIG. 24a is a top perspective view of the lancing device of FIG. 17, showing the slider being pulled from the retracted position to the extended position to initiate a process for removing a spent cartridge after all the lancets have been used.
Figure 24D:
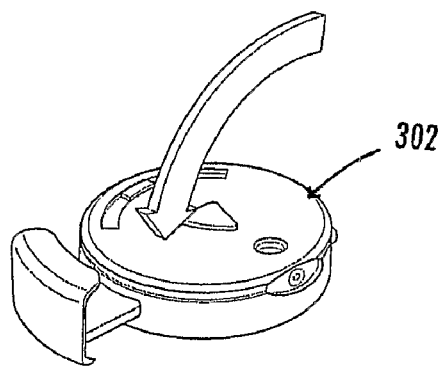
FIG. 24*d* is a top perspective view of the lancing device of FIG. 24*a*, showing the housing being closed.
Figure 24B:
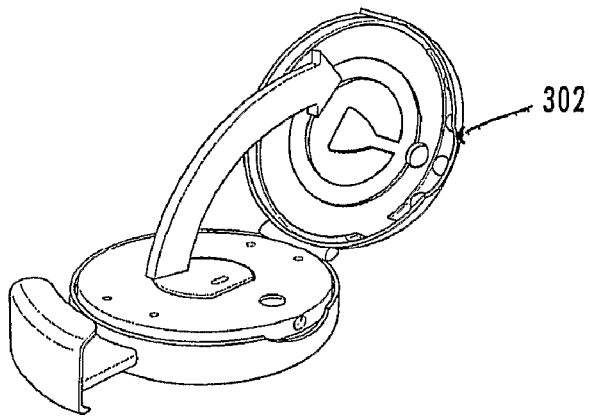
FIG. 24b is a top perspective view of the lancing device of FIG. 24a, showing the housing being opened.
Figure 24E:
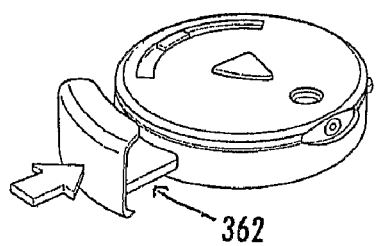
FIG. 24*e* is a top perspective view of the lancing device of FIG. 24*a*, showing the slider being pushed back in to its retracted position.
Figure 24C:
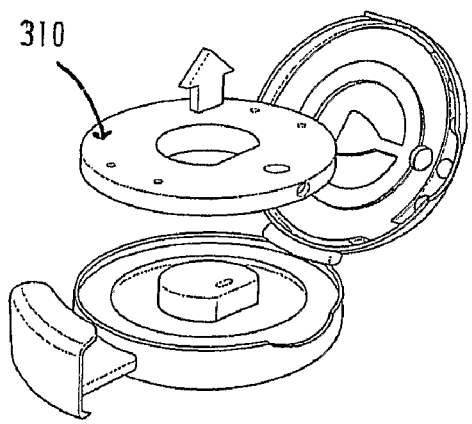
FIG. 24c is a top perspective view of the lancing device of FIG. 24a, showing the spent cartridge being removed from the housing.

FIGS. 24a-24e illustrate a process for removing a spent cartridge 310 after each of the lancets have been sequentially advanced to the active position and used. In FIG. 24a, the slider 362 of the advancer mechanism 360 is being pulled from the retracted position to the extended position to unlock the housing 302. In FIG. 24b, the housing 302 is being opened. In FIG. 24c, the spent cartridge 310 is being removed from the housing 302. If desired, a new cartridge 310 can now be inserted into the housing 302 for use. Otherwise, in FIG. 24d the housing 302 is closed for now, and in FIG. 24e, the slider 362 is pushed back in to its retracted position to relock the housing. Then a new cartridge 310 can later be inserted according to the process shown in FIGS. 22a-22f.

Figure 25A:
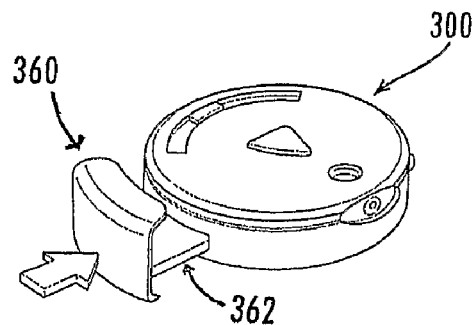
FIG. 25*a* is a top perspective view of the lancing device of FIG. 17, showing the slider being pulled from the retracted position to the extended position to initiate a process for removing a partially spent cartridge before all of the lancets have been used.
Figure 25D:
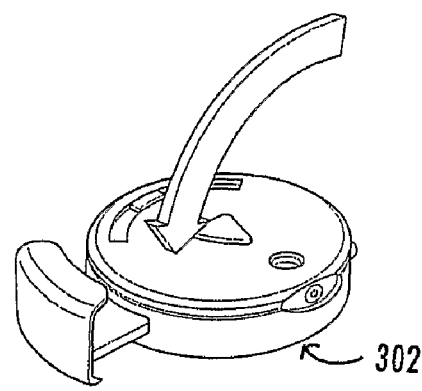
FIG. 25*d* is a top perspective view of the lancing device of FIG. 25*a*, showing the housing being closed.
Figure 25B:
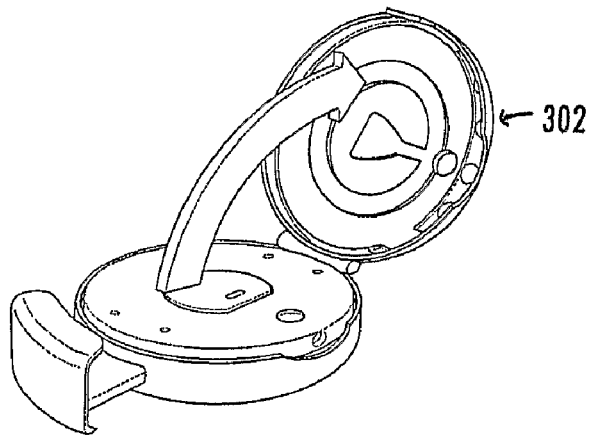
FIG. 25*b* is a top perspective view of the lancing device of FIG. 25*a*, showing the housing being opened.
Figure 25E:
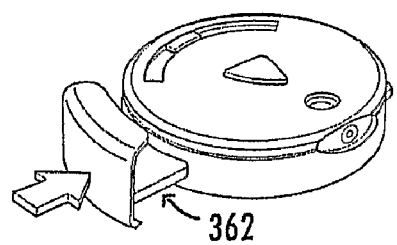
FIG. 25*e* is a top perspective view of the lancing device of FIG. 25*a*, showing the slider being pushed back in to its retracted position.
Figure 25C:
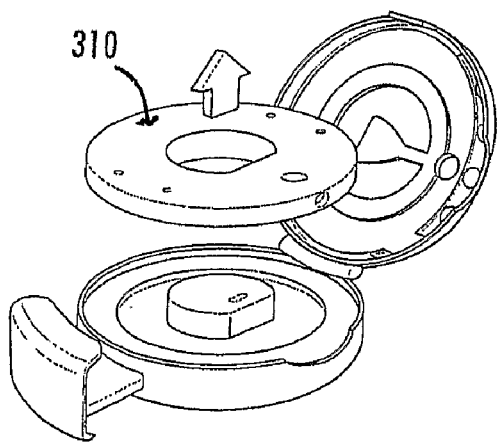
FIG. 25*c* is a top perspective view of the lancing device of FIG. 25*a*, showing the partially spent cartridge being removed from the housing.

FIGS. 25a-25e illustrate a process for removing a partially spent cartridge 310 before all of its lancets have been used. In FIG. 25a, the slider 362 of the advancer mechanism 360 is being pulled from the retracted position to the extended position to unlock the housing 302. In FIG. 25b, the housing 302 is being opened. In FIG. 25c, the partially spent cartridge 310 is being removed from the housing 302. In FIG. 25d, the housing 302 is being closed. And in FIG. 25e, the slider 362 is being pushed back in to its retracted position to relock the housing 302.

Figure 26A:
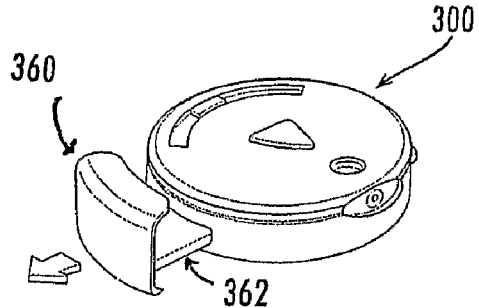
FIG. 26*a* is a top perspective view of the lancing device of FIG. 17, showing the slider being pulled from the retracted position to the extended position to initiate a process for reinserting the partially spent cartridge that was removed prior to all of the lancets being used.
Figure 26D:
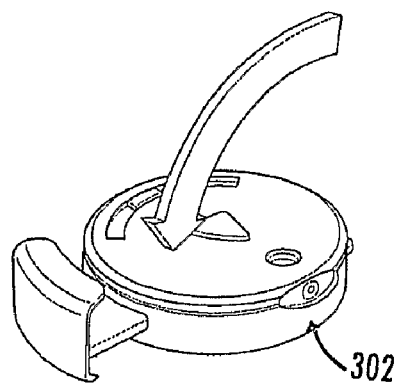
FIG. 26*d* is a top perspective view of the lancing device of FIG. 26*a*, showing the housing being closed.
Figure 26B:
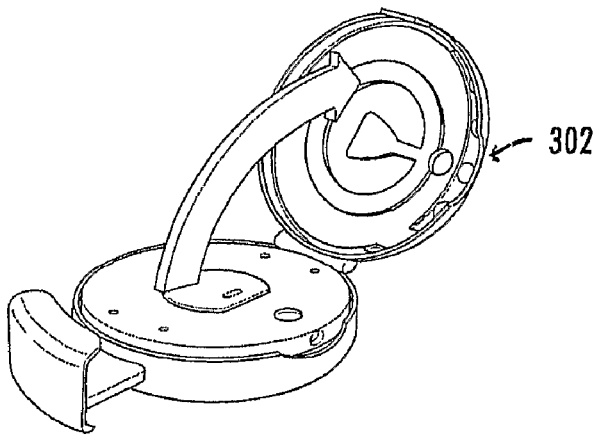
FIG. 26*b* is a top perspective view of the lancing device of FIG. 26*a*, showing the housing being opened.
Figure 26E:
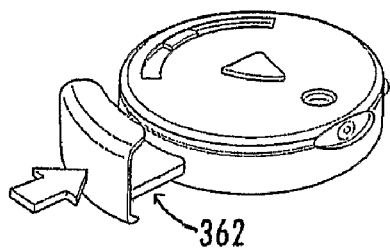
FIG. 26*e* is a top perspective view of the lancing device of FIG. 26*a*, showing the slider being pushed back in to its retracted position.
Figure 26C:
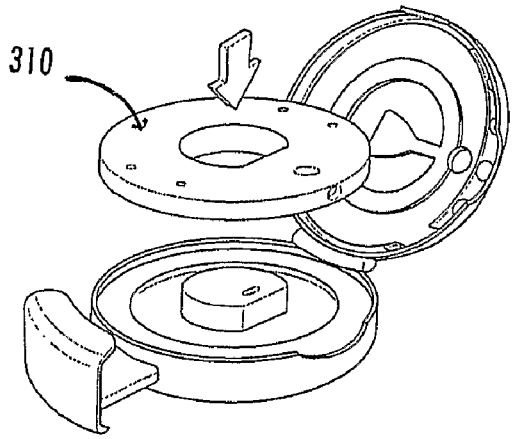
FIG. 26*c* is a top perspective view of the lancing device of FIG. 26*a*, showing the partially spent cartridge being reinserted into the housing.
Figure 26F:
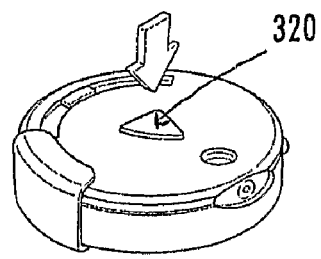
FIG. 26*f* is a top perspective view of the lancing device of FIG. 26*a*, showing the activating button being pressed to activate the lancing device.

FIGS. 26a-26f illustrate a process for later reinserting the partially spent cartridge 310 that was removed prior to all of its lancets being used. In FIG. 26a, the slider 362 of the advancer mechanism 360 is being pulled from the retracted position to the extended position to unlock the housing 302. In FIG. 26b, the housing 302 is being opened. In FIG. 26c, the partially spent cartridge 310 is being reinserted into the housing 302. In FIG. 26d, the housing 302 is being closed. In FIG. 26e, the slider 362 is being pushed back in to its retracted position to relock the housing 302. And in FIG. 26f, the activating button 320 is being pressed to activate the lancing device 300 for lancing with the then-active lancet. Of course, a new cartridge 310 can instead be inserted according to the process shown in FIGS. 22a-22f.

Figure 27A:
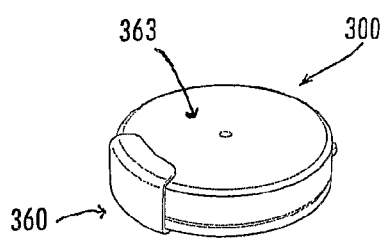
FIG. 27*a* is a bottom perspective view of the lancing device of FIG. 17, showing a fail-safe release of the advancer mechanism being activated to initiate a process for clearing the lancing device if it becomes jammed.
Figure 27D:
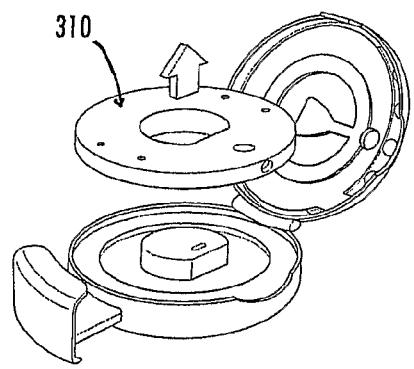
FIG. 27*d* is a top perspective view of the lancing device of FIG. 27*a*, showing the cartridge being removed from the housing.
Figure 27B:
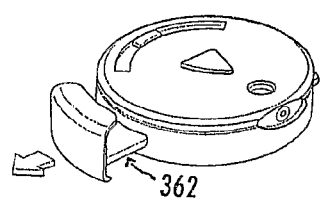
FIG. 27*b* is a top perspective view of the lancing device of FIG. 27*a*, showing the slider being pulled from its retracted position to its extended position.
Figure 27E:
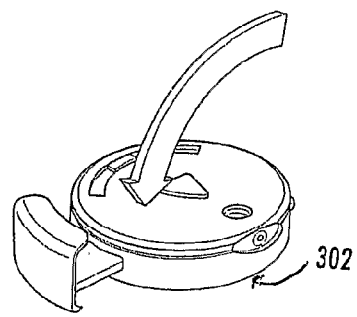
FIG. 27*e* is a top perspective view of the lancing device of FIG. 27*a*, showing the housing being closed.
Figure 27C:
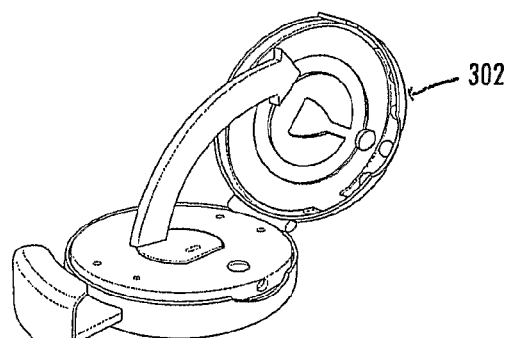
FIG. 27*c* is a top perspective view of the lancing device of FIG. 27*a*, showing the housing being opened.
Figure 27F:
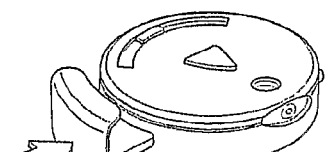
FIG. 27*f* is a top perspective view of the lancing device of FIG. 27*a*, showing the slider being pushed back in to its retracted position.
Figure 29:
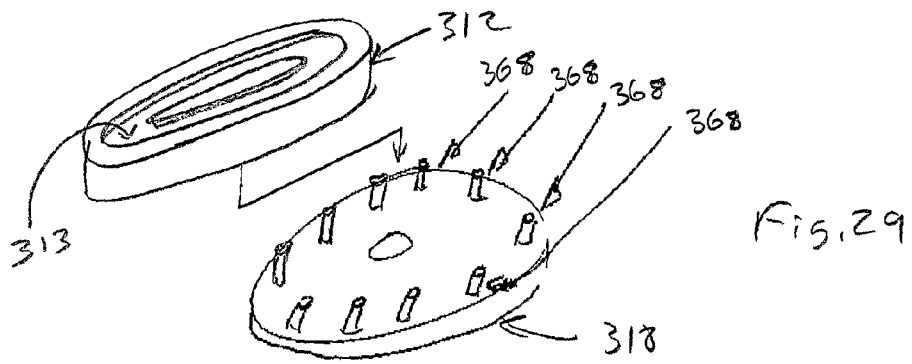
FIG. 29 is a perspective bottom view of the carrier of the lancet cartridge of the lancing device of FIG. 17, showing ratchet teeth of an indexing ratchet mechanism of the advancer mechanism.

FIGS. 27a-27f illustrate a process for clearing the lancing device 300 if it becomes jammed. In FIG. 27a, a fail-safe release mechanism 363 of the advancer mechanism 360 is being activated to release the advancer mechanism. Preferably, the fail-safe release mechanism 363 includes a small opening in the housing 302 through which a thin elongated object (i.e., a paper clip wire or a pen tip) can be inserted to engage a release that frees the slider 362 for movement. In FIG. 27b, the slider 362 is being pulled from its retracted position to its extended position to unlock the housing 302. In FIG. 27c, the housing 302 is being opened. In FIG. 27d, the jammed lancet cartridge 310 is being removed from the housing. In FIG. 27e, the housing is being closed. And in FIG. 27f, the slider 362 is being pushed back in to its retracted position to relock the housing 302. A new lancet cartridge 310 now may be inserted according to the process shown in FIGS. 22a-22f, or this may be done before closing the housing 302.

Figure 28:
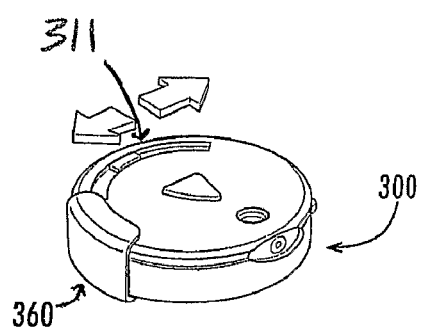
FIG. 28 is a top perspective view of the lancing device of FIG. 17, showing the use of the depth adjustment mechanism to set the lancing puncture depth.

FIG. 28 shows the use of the depth adjustment mechanism 311 to set the lancing puncture depth. The depth adjustment mechanism 311 may include the depth-control ring 212 shown in FIG. 13 or another conventional mechanism for selectively controlling the puncture depth of the lancets.

While the invention has been described with reference to preferred and example embodiments, it will be understood by those skilled in the art that a variety of modifications, additions and deletions are within the scope of the invention, as defined by the following claims.

What is claimed is:

1. A lancing device for use with a cartridge assembly having an array of lancets, each lancet including a detachable cap, the lancing device comprising:
   a housing for receiving the cartridge assembly;
   an indexing ratchet mechanism adapted to sequentially advance the lancets into an active lancet position;
   a drive mechanism having a drive member adapted to engage and retract an active-positioned one of the lancets to detach the corresponding active-positioned cap, and to drive the active-positioned lancet along a lancing stroke;
   a charger mechanism adapted to retract the drive member;
   a cap displacement mechanism adapted to engage and move the active-positioned, detached lancet cap from the lancing stroke path of the active-positioned lancet; and a slider that is slidable relative to the housing and adapted to actuate the indexing ratchet mechanism, the charger mechanism, and the cap displacement mechanism as the slider is moved between a first position and a second position.

2. The lancing device of claim 1, wherein the cartridge assembly includes ratchet teeth, and wherein the indexing ratchet mechanism includes a resiliently deflectable pawl extending from the slider that engages the ratchet teeth to advance the lancets in the cartridge to the active position.

3. The lancing device of claim 1, wherein the charger mechanism includes a resiliently deflected cam arm that extends from the slider and is adapted to retract the drive member.

4. The lancing device of claim 3, wherein the drive member has a charging follower and the cam arm is resiliently deflected by the charging follower when the slider is moved from the first position toward the second position.

5. The lancing device of claim 4, wherein the cam arm is moved past the charging follower when the slider reaches the second position, and the cam arm returns to its neutral position.

6. The lancing device of claim 5, wherein the cam arm engages the charging follower and retracts the drive member as the slider is moved from the second position back to the first position.

7. The lancing device of claim 3, wherein the drive member has a locking follower and the slider defines a locking wall that blocks a travel path of the drive member locking follower except when the slider is in the second position.

8. The lancing device of claim 3, wherein the lancet cap is detached from the active lancet when the drive member retracts the lancet.

9. The lancing device of claim 8, wherein the slider includes a cam surface and the cap displacement mechanism includes a lifter with a follower that is guided by the cam surface to move a separated lancet cap from the lancing stroke path of the active lancet when the slider is moved from the second position to the first position.

10. The lancing device of claim 1, wherein the slider includes a cam surface and the cap displacement mechanism includes a lifter with a follower that is guided by the cam surface to move a separated lancet cap from the lancing stroke path of the active lancet when the slider is moved from the second position to the first position.

11. The lancing device of claim 10, wherein the cam surface is configured so that, during a first part of the slider movement from the second position to the first position, the lifter is in a lowered position so that the lifter is out of the way of the lancets being advanced out of and into the active position and so that the active lancet can be retracted to detach the cap of the active lancet, and during a second part of the slider movement from the second position to the first position, the lifter is raised to engage and move the detached cap out of the way of the lancet stroke path.

12. The lancing device of claim 11, further comprising a lifter guide track for guiding the raising and lowering movement of the lifter.

13. The lancing device of claim 10, wherein the lifter defines an opening through which the lancet passes during the lancing stroke.

14. The lancing device of claim 1 further comprising a multi-lancet cartridge removably installed within the housing.

15. A lancing device for use with a cartridge assembly having an array of lancets sequentially advanced to an active position, the lancing device comprising:

a housing for receiving the cartridge assembly;
a drive mechanism having a drive member adapted to engage and retract an active-positioned one of the lancets to an armed position and to drive the active-positioned lancet along a lancing stroke; and
a cam-guided charger mechanism adapted to retract the drive member,
wherein the active lancet is capped by an active lancet cap that is detached from the active lancet by the drive member retracting the lancet.

16. The lancing device of claim 15, further comprising a slider that is slidable relative to the housing and adapted to actuate the cam-guided charger mechanism as the slider is moved between a first position and a second position.

17. The lancing device of claim 16, wherein the charger mechanism includes a resiliently deflected cam arm that extends from the slider and is adapted to retract the drive member.

18. The lancing device of claim 17, wherein the drive member has a charging follower and the cam arm is resiliently deflected by the charging follower when the slider is moved from the first position toward the second position.

19. The lancing device of claim 18, wherein the cam arm is moved past the charging follower when the slider reaches the second position, and the cam arm returns to its neutral position.

20. The lancing device of claim 19, wherein the cam arm engages the charging follower and retracts the drive member as the slider is moved from the second position back to the first position.

21. The lancing device of claim 16, wherein the drive member has a locking follower and the slider defines a locking wall that blocks a travel path of the drive member locking follower except when the slider is in the second position.

22. The lancing device of claim 15, further comprising an indexing ratchet mechanism adapted to sequentially advance the lancets and a cam-guided cap displacement mechanism adapted to move detached lancet caps out of the active lancet lancing stroke path.

23. A lancing device for use with a cartridge assembly having an array of lancets, each lancet including a detachable cap, the lancing device comprising:

a housing for receiving the cartridge assembly;
a drive mechanism having a drive member adapted to engage and retract an active-positioned one of the lancets to detach the corresponding active-positioned cap, and to drive the active-positioned lancet along a lancing stroke; and
a cam-guided cap displacement mechanism adapted to engage and move the active-positioned, detached lancet cap from the lancing stroke path of the active-positioned lancet,
wherein the lancet cap is separated from the active lancet when the drive member retracts the lancet.

24. The lancing device of claim 23, further comprising a slider that is slidable relative to the housing and adapted to actuate the cap displacement mechanism as the slider is moved between a first position and a second position.

25. The lancing device of claim 23, wherein the slider includes a cam surface and the cap displacement mechanism includes a lifter with a follower that is guided by the cam surface to moving the detached lancet cap from the lancing stroke path of the active lancet when the slider is moved from the second position to the first position.

26. The lancing device of claim 25, wherein the cam surface is configured so that, during a first part of the slider movement from the second position to the first position, the lifter is in a lowered position so that the lifter is out of the way of the lancets being advanced out of and into the active position and so that the active lancet can be retracted to detach the cap of the active lancet, and during a second part of the slider movement from the second position to the first position, the lifter is raised to engage and move the detached cap out of the way of the lancet stroke path.

27. The lancing device of claim 25, further comprising a lifter guide track for guiding the raising and lowering movement of the lifter.

28. The lancing device of claim 25, wherein the lifter defines an opening through which the lancet passes during the lancing stroke.

29. The lancing device of claim 23, further comprising an indexing ratchet mechanism adapted to sequentially advance the lancets and a cam-guided charging mechanism adapted to retract the drive member.

* * * * *